United States Patent
Sullivan et al.

(10) Patent No.: US 11,602,318 B2
(45) Date of Patent: Mar. 14, 2023

(54) MOBILE ANATOMICAL IMAGING SYSTEM WITH IMPROVED MOVEMENT SYSTEM

(71) Applicant: NeuroLogica Corporation, a subsidiary of Samsung Electronics Co., Ltd., Danvers, MA (US)

(72) Inventors: Philip Sullivan, Danvers, MA (US); Henry Cholod, Tewksbury, MA (US); Michael Limoli, Merrimac, MA (US); Marshal Doughty, Weymouth, MA (US); Alexander Baval, Somerville, MA (US); Richard DeSalvo, Danvers, MA (US)

(73) Assignee: NeuroLogics Corporation, a subsidiary of Samsung Electronics Co., Ltd., Danvers, MA (US)

( * ) Notice: Subject to any disclaimer, the term of this patent is extended or adjusted under 35 U.S.C. 154(b) by 0 days.

(21) Appl. No.: 16/909,680

(22) Filed: Jun. 23, 2020

(65) Prior Publication Data
US 2021/0145381 A1 May 20, 2021

Related U.S. Application Data

(63) Continuation of application No. 15/908,341, filed on Feb. 28, 2018, now Pat. No. 10,687,770.
(Continued)

(51) Int. Cl.
*A61B 6/00* (2006.01)
*A61B 6/03* (2006.01)
(Continued)

(52) U.S. Cl.
CPC ............ *A61B 6/4405* (2013.01); *A61B 6/027* (2013.01); *A61B 6/032* (2013.01); *A61B 6/105* (2013.01); *A61B 6/547* (2013.01); *B60B 19/003* (2013.01)

(58) Field of Classification Search
None
See application file for complete search history.

(56) References Cited

U.S. PATENT DOCUMENTS

| 4,708,420 A | 11/1987 | Liddiard |
| 6,131,690 A | 10/2000 | Galando et al. |
(Continued)

FOREIGN PATENT DOCUMENTS

| CN | 202061023 | 12/2011 |
| CN | 202443134 | 9/2012 |
(Continued)

OTHER PUBLICATIONS

Munakata, Yu et al., An Active-caster Drive System for Motorizing a Manual Wheelchair, Proceedings of 2013 IEEE, International Conference on Mechatronics and Automation, Takamatsu, Japan, 2013.

*Primary Examiner* — Hoon K Song
(74) *Attorney, Agent, or Firm* — Pandiscio & Pandiscio

(57) ABSTRACT

A new and improved anatomical imaging system which includes a new and improved movement system, wherein the movement system comprises an omnidirectional powered drive unit and wherein the movement system can substantially eliminate lateral walk (or drift) over the complete stroke of a scan, even when the floor includes substantial irregularities, whereby to improve the accuracy of the scan results and avoid unintentional engagement of the anatomical imaging system with the bed or gurney which is supporting the patient.

18 Claims, 28 Drawing Sheets

Related U.S. Application Data

(60) Provisional application No. 62/597,299, filed on Dec. 11, 2017, provisional application No. 62/464,486, filed on Feb. 28, 2017.

(51) Int. Cl.
    *A61B 6/10* (2006.01)
    *A61B 6/02* (2006.01)
    *B60B 19/00* (2006.01)

(56) References Cited

U.S. PATENT DOCUMENTS

| | | |
|---|---|---|
| 6,374,937 B1 | 4/2002 | Galando et al. |
| 6,857,778 B2 | 2/2005 | Mun et al. |
| 8,718,898 B2 | 5/2014 | Schaible |
| 9,554,953 B2 | 1/2017 | Dirauf et al. |
| 9,770,943 B2 | 9/2017 | Liddiard |
| 2003/0034687 A1 | 2/2003 | Harris |
| 2003/0095635 A1 | 5/2003 | Moritake et al. |
| 2005/0030604 A1 | 2/2005 | Moore |
| 2010/0180380 A1 | 7/2010 | Van Scheppingen et al. |
| 2010/0299014 A1 | 11/2010 | Bouvier |
| 2012/0181846 A1 | 7/2012 | Liddiard |
| 2013/0292918 A1 | 11/2013 | Schlee et al. |
| 2013/0340167 A1 | 12/2013 | Karwal et al. |
| 2014/0251702 A1 | 9/2014 | Berger et al. |
| 2015/0051519 A1 | 2/2015 | Morbi et al. |
| 2015/0085992 A1 | 3/2015 | Grady |
| 2015/0196263 A1* | 7/2015 | Bailey .................. G01N 23/046 378/20 |
| 2016/0242705 A1 | 8/2016 | Richardson |
| 2017/0215826 A1* | 8/2017 | Johnson ............... H02G 11/006 |
| 2017/0325763 A1* | 11/2017 | Hoernig ............... A61B 6/4417 |
| 2018/0014796 A1* | 1/2018 | Stanton .................. A61B 6/035 |
| 2019/0099141 A1 | 4/2019 | Garlow et al. |

FOREIGN PATENT DOCUMENTS

| | | |
|---|---|---|
| DE | 10 2016 208 123 | 9/2017 |
| WO | WO 2016/066436 | 5/2016 |
| WO | WO 2017/180566 | 10/2017 |
| WO | WO 2017/180568 | 10/2017 |
| WO | WO 2017/180569 | 10/2017 |
| WO | WO 2017/180570 | 10/2017 |

\* cited by examiner

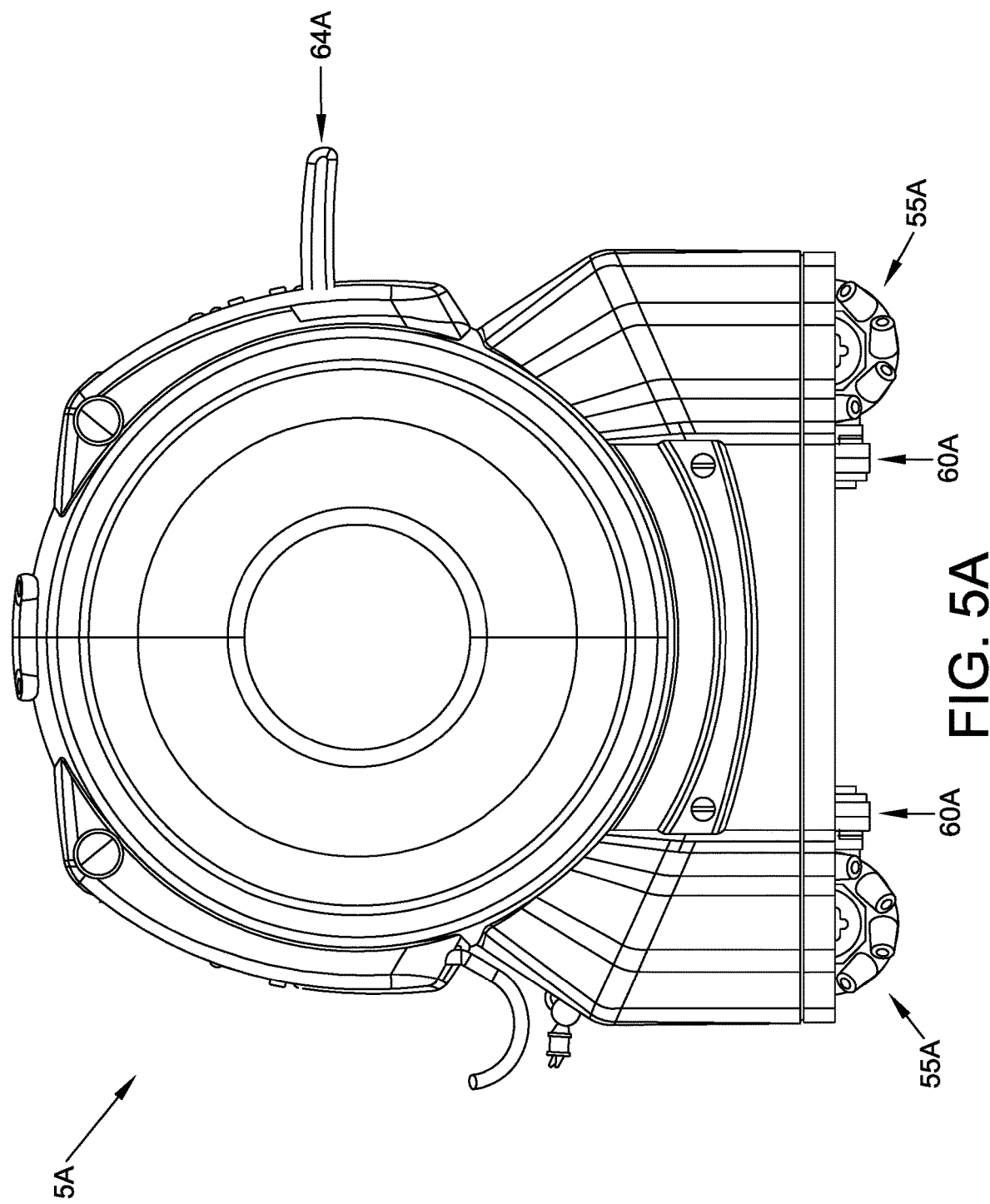

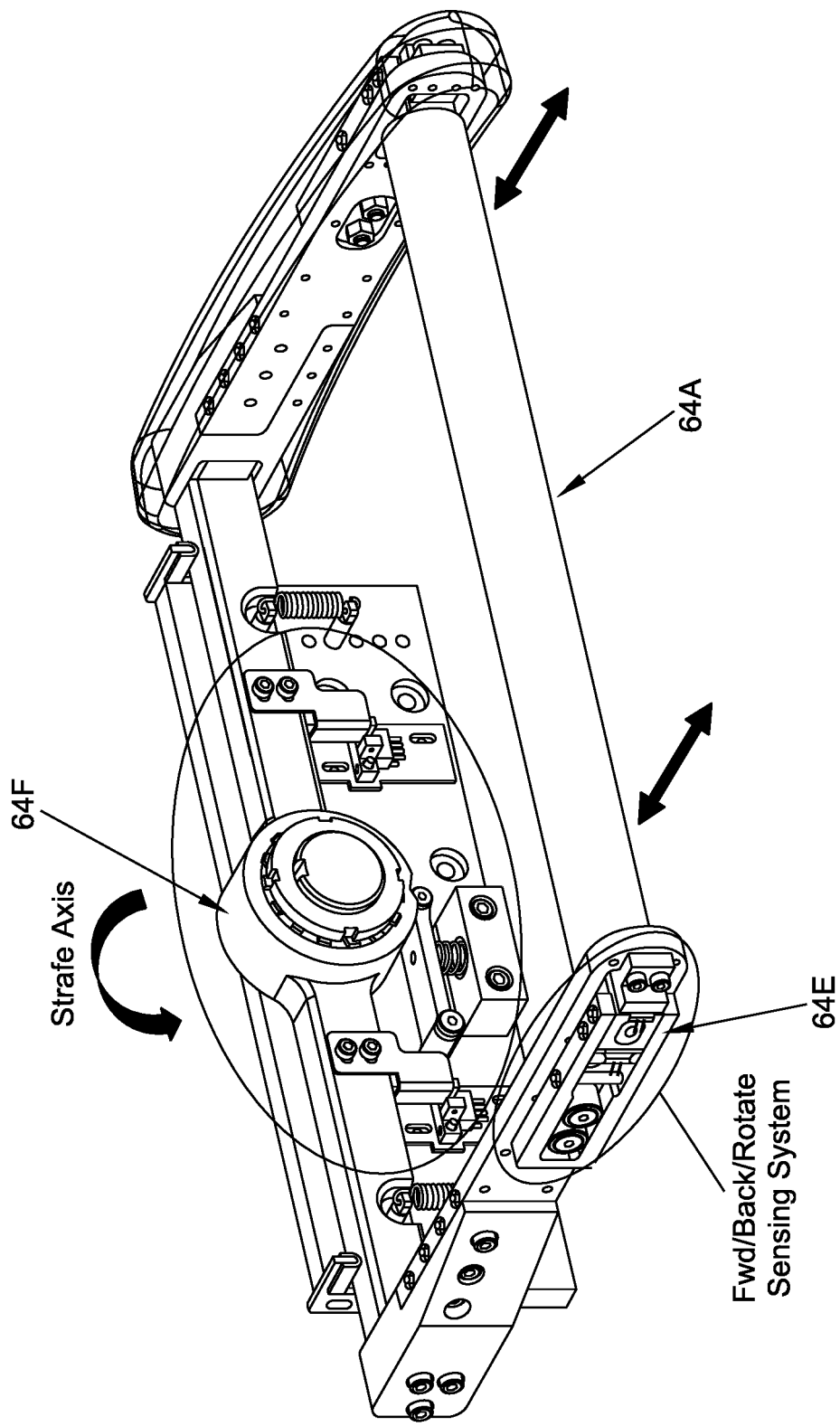

MOBILE ANATOMICAL IMAGING SYSTEM WITH IMPROVED MOVEMENT SYSTEM

REFERENCE TO PRIOR PATENT APPLICATIONS

This patent application is a continuation of prior U.S. patent application Ser. No. 15/908,341, filed Feb. 28, 2018 by NeuroLogica Corporation, a subsidiary of Samsung Electronics Co., Ltd. for MOBILE ANATOMICAL IMAGING SYSTEM WITH IMPROVED MOVEMENT SYSTEM, which patent application in turn claims benefit of:

(i) prior U.S. Provisional Patent Application Ser. No. 62/464,486, filed Feb. 28, 2017 by NeuroLogica Corporation, a subsidiary of Samsung Electronics Co., Ltd., and Phillip Sullivan et al. for ANATOMICAL IMAGING SYSTEM WITH OMNIDIRECTIONAL POWERED DRIVE UNIT; and (ii) prior U.S. Provisional Patent Application Ser. No. 62/597,299, filed Dec. 11, 2017 by NeuroLogica Corporation, a subsidiary of Samsung Electronics Co., Ltd., and Phillip Sullivan et al. for MOBILE ANATOMICAL IMAGING SYSTEM WITH IMPROVED MOVEMENT SYSTEM.

The three (3) above-identified patent applications are hereby incorporated herein by reference.

FIELD OF THE INVENTION

This invention relates to imaging systems in general, and more particularly to mobile anatomical imaging systems with powered drive units.

BACKGROUND OF THE INVENTION

In many situations it can be desirable to image the interior of opaque objects. By way of example but not limitation, in the medical field, it can be desirable to image the interior of a patient's body so as to allow viewing of internal structures without physically penetrating the skin.

Computerized Tomography (CT) has emerged as a key imaging modality in the medical field. CT imaging systems generally operate by directing X-rays into the body from a variety of positions, detecting the X-rays passing through the body, and then processing the detected X-rays so as to build a three-dimensional (3D) data set of the patient's anatomy. This 3D data set can then be processed so as to create a 3D computer model of the patient's anatomy. The 3D data set and 3D computer model can then be visualized so as to provide images (e.g., slice images, 3D computer images, etc.) of the patient's anatomy.

By way of example but not limitation, and looking now at FIGS. 1 and 2, there is shown an exemplary CT imaging system 5. CT imaging system 5 generally comprises a torus 10 which is supported by a base 15. A center opening 20 is formed in torus 10. Center opening 20 receives the patient anatomy which is to be scanned.

Looking next at FIG. 3, torus 10 generally comprises a fixed gantry 22, a rotating disc 23, an X-ray tube assembly 25 and an X-ray detector assembly 30. More particularly, fixed gantry 22 is disposed concentrically about center opening 20. Rotating disc 23 is rotatably mounted to fixed gantry 22. X-ray tube assembly 25 and X-ray detector assembly 30 are mounted to rotating disc 23 in diametrically-opposing relation, such that an X-ray beam 40 (generated by X-ray tube assembly 25 and detected by X-ray detector assembly 30) is passed through the patient anatomy disposed in center opening 20. Inasmuch as X-ray tube assembly 25 and X-ray detector assembly 30 are mounted on rotating disc 23 so that they are rotated concentrically about center opening 20, X-ray beam 40 will be passed through the patient's anatomy along a full range of radial positions, so as to enable CT imaging system 5 to create a "slice" image of the anatomy penetrated by the X-ray beam. Furthermore, by moving the patient and CT imaging system 5 relative to one another during scanning, a series of slice images can be acquired, and thereafter appropriately processed, so as to create a 3D data set of the scanned anatomy. This 3D data set can then be processed so as to create a 3D computer model of the scanned anatomy. In practice, it is common to configure X-ray detector assembly 30 so that multiple slices of images (e.g., 8 slices, 16 slices, 32 slices, etc.) may be acquired with each rotation of rotating disc 23, whereby to speed up the acquisition of scan data.

In practice, it is now common to effect helical scanning of the patient's anatomy so as to generate a 3D data set of the scanned anatomy, which can then be processed so as to create a 3D computer model of the scanned anatomy. The 3D data set and 3D computer model can then be visualized so as to provide images (e.g., slice images, 3D computer images, etc.) of the patient's anatomy.

The various electronic hardware and software for controlling the operation of rotating disc 23, X-ray tube assembly 25 and X-ray detector assembly 30, as well as for processing the acquired scan data so as to generate the desired slice images, 3D data set and 3D computer model, may be of the sort well known in the art and may be located in torus 10 and/or base 15.

In many cases CT imaging system 5 is intended to be stationary, in which case base 15 of CT imaging system 5 is set in a fixed position on the floor of a room and a special motorized bed is provided to move the patient relative to CT imaging system 5 during scanning. More particularly, with a stationary CT imaging system 5, the patient is brought to the location of CT imaging system 5, the patient is placed on the special motorized bed, and then the motorized bed is used to move the patient relative to CT imaging system 5 (i.e., to advance the patient into center opening 20 of CT imaging system 5) so that some or all of the length of the patient may be scanned by CT imaging system 5.

In other cases CT imaging system 5 is intended to be mobile so that the CT imaging system may be brought to the patient and the patient scanned at the patient's current location, with the CT imaging system moving relative to the patient during scanning. Scanning the patient with a mobile CT imaging system 5 can be highly advantageous, since it can reduce delays in patient scanning (e.g., the patient can be scanned in an emergency room rather than waiting to be transported to the radiology department) and/or it can allow the patient to be scanned without requiring movement of the patient (e.g., the patient can be scanned at their bedside in an intensive care unit, "ICU").

To this end, and looking now at FIGS. 4 and 5, base 15 may comprise a transport assembly 50 for (i) moving mobile CT imaging system 5 to the location of the patient prior to scanning, and (ii) moving the CT imaging system relative to the patient during scanning. More particularly, transport assembly 50 preferably comprises (i) a gross movement mechanism 55 for moving CT imaging system 5 relatively quickly across room distances, so that the CT imaging system can be quickly and easily brought to the bedside of the patient, such that the patient can be scanned at their bedside without needing to be moved to a radiology department, and (ii) a fine movement mechanism 60 for moving the CT imaging system precisely, relative to the patient, during scanning so that the patient can be scanned on their bed or gurney without needing to be moved onto a special motorized bed.

In one preferred form of the invention, gross movement mechanism 55 preferably comprises a plurality of free-rolling casters 62, and fine movement mechanism 60 preferably comprises a plurality of centipede belt drives 63 (which can be configured for either stepped or continuous motion, whereby to provide either stepped or continuous scanning of the patient). Hydraulic apparatus 65 permits either gross movement mechanism 55 or fine movement mechanism 60 to be engaged with the floor, whereby to facilitate appropriate movement of mobile CT imaging system 5.

Thus, with a mobile CT imaging system 5, the mobile CT imaging system may be pre-positioned in an "out of the way" location (e.g., in an unused corner of an emergency room) and then, when a patient requires scanning, the patient may be quickly and easily scanned at their bedside, by simply moving the mobile CT imaging system to the patient's bedside on gross movement mechanism 55 (e.g., on casters 62), and thereafter moving the mobile CT imaging system during scanning on fine movement mechanism 60 (e.g., on centipede belt drives 63).

However, it has been found that where the mobile CT imaging system becomes larger (e.g., such as where the mobile CT imaging system is sized for full-body scans), using free-rolling castors 62 for gross movement mechanism 55 can become problematic. By way of example but not limitation, where the mobile CT imaging system is sized for full-body scans, the mobile CT imaging system can weigh thousands of pounds and it can require substantial effort to physically push the mobile CT imaging system down corridors and across rooms when the mobile CT imaging system is supported on free-rolling castors. Furthermore, where the mobile CT imaging system is sized for full-body scans, it can be difficult to maneuver the mobile CT imaging system when it is supported on free-rolling castors, e.g., such as when the mobile CT imaging system must be maneuvered around a corner in a hospital corridor.

In addition to the foregoing, it has also been found that where the floor of the medical facility has substantial irregularities (e.g., bumps, recesses, etc.), centipede belt drives 63 of mobile CT imaging system 5 may not uniformly contact the floor over the complete "stroke" of the scan. When this occurs, mobile CT imaging system 5 may not move uniformly over the full stroke of the scan, which can affect the accuracy of the scan results.

Among other things, mobile CT imaging system 5 may shift (i.e., "drift") laterally during its scan stroke, then shift further laterally during its return stroke, then shift further laterally during its next scan stroke, then shift further laterally during its next return stroke, etc.

Over long scan strokes (e.g., such as is the case with "full body" scans), and/or with repeated scan strokes (e.g., such as is the case where numerous scans must be taken), such lateral "walking" (or "drifting") of CT imaging system 5 may create issues with scan quality.

Furthermore, since CT imaging system 5 is moving independently of the bed or gurney which is supporting the patient, there is also the possibility that, after repeated long scan strokes, CT imaging system 5 may walk (or drift) so far laterally that the CT imaging system bumps into the bed or gurney which is supporting the patient.

Thus, there is a need for a new and improved movement system for a mobile CT imaging system which can facilitate movement and maneuvering of the mobile CT imaging system when moving the mobile CT imaging system between scanning locations, and which can substantially eliminate lateral walk (or drift) over the complete stroke of a scan during scanning, even when the floor includes substantial irregularities, whereby to improve the accuracy of the scan results and avoid unintentional engagement of the CT imaging system with the bed or gurney which is supporting the patient.

SUMMARY OF THE INVENTION

These and other objects of the present invention are addressed by the provision and use of a new and improved anatomical imaging system which includes a new and improved movement system.

In one form of the invention, the anatomical imaging system comprises a gross movement mechanism in the form of an omnidirectional drive unit, and a fine movement mechanism in the form of powered wheels (also sometimes referred to herein as "motorized wheels"), and wherein the fine movement mechanism can substantially eliminate lateral walk (or drift) over the complete stroke of the scan, even where the floor includes substantial irregularities, whereby to improve the accuracy of the scan results and avoid unintentional engagement of the anatomical imaging system with the bed or gurney which is supporting the patient.

In another form of the invention, the anatomical imaging system comprises an omnidirectional powered drive unit for moving the anatomical imaging system during both (i) movement between scanning locations and (ii) during scanning, wherein the omnidirectional powered drive unit can facilitate movement and maneuvering of the mobile CT imaging system when moving the mobile CT imaging system between scanning locations, and wherein the omnidirectional powered drive unit can substantially eliminate lateral walk (or drift) over the complete stroke of the scan, even when the floor includes substantial irregularities, whereby to improve the accuracy of the scan results and avoid unintentional engagement of the anatomical imaging system with the bed or gurney which is supporting the patient.

In one preferred form of the invention, there is provided an imaging system comprising:
  a scanner; and
  a transport mechanism mounted to the base of the scanner, wherein the transport mechanism comprises:
    a gross movement mechanism for transporting the scanner relatively quickly across room distances; and
    a fine movement mechanism for moving the scanner precisely, relative to the object being scanned, during scanning; and
    apparatus for selectively causing the gross movement mechanism or the fine movement mechanism to engage the floor;
    wherein the gross movement mechanism comprises a plurality of wheels configured to provide omnidirectional drive; and
    wherein the fine movement mechanism comprises a plurality of independently powered wheels.

In another preferred form of the invention, there is provided a method for scanning an object, the method comprising:
  providing an imaging system, the imaging system comprising:
    a scanner; and a transport mechanism mounted to the base of the scanner, wherein the transport mechanism comprises:
  a gross movement mechanism for transporting the scanner relatively quickly across room distances; and
  a fine movement mechanism for moving the scanner precisely, relative to the object being scanned, during scanning; and
  apparatus for selectively causing the gross movement mechanism or the fine movement mechanism to engage the floor;
  wherein the gross movement mechanism comprises a plurality of wheels configured to provide omnidirectional drive; and
  wherein the fine movement mechanism comprises a plurality of independently powered wheels;
transporting the scanner to the object, across room distances, using the gross movement mechanism; and
while moving the scanner precisely, relative to the object, with the fine movement mechanism, scanning the object.

In another preferred form of the invention, there is provided an imaging system comprising:
a scanner; and
a transport mechanism mounted to the base of the scanner, wherein the transport mechanism is configured to (i) transport the scanner relatively quickly across room distances, and (ii) move the scanner precisely, relative to the object being scanned, during scanning, wherein the transport mechanism comprises a plurality of wheels configured to provide omnidirectional drive.

In another preferred form of the invention, there is provided a method for scanning an object, the method comprising:
providing an imaging system, the imaging system comprising:
  a scanner; and
  a transport mechanism mounted to the base of the scanner, wherein the transport mechanism is configured to (i) transport the scanner relatively quickly across room distances, and (ii) move the scanner precisely, relative to the object being scanned, during scanning, wherein the transport mechanism comprises a plurality of wheels configured to provide omnidirectional drive;
transporting the scanner to the object, across room distances, using the transport mechanism; and
while moving the scanner precisely, relative to the object, with the transport mechanism, scanning the object.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Novel Mobile CT Imaging System Comprising a Gross Movement Mechanism in The Form of an Omnidirectional Drive Unit, and a Fine Movement Mechanism in the Form of Powered Wheels In accordance with the present invention, there is provided a new and improved anatomical imaging system (e.g., a mobile CT imaging system) which includes a new and improved movement system which comprises a gross movement mechanism in the form of an omnidirectional drive unit, and a fine movement mechanism in the form of powered wheels. As will hereinafter be discussed, the omnidirectional drive unit facilitates movement and maneuvering of the mobile CT imaging system when moving the mobile CT imaging system between scanning locations, and the powered wheels can substantially eliminate lateral walk (or drift) over the complete stroke of a scan during scanning, even when the floor includes substantial irregularities, whereby to improve the accuracy of the scan results and avoid unintentional engagement of the CT imaging system with the bed or gurney which is supporting the patient.

Figure 1:
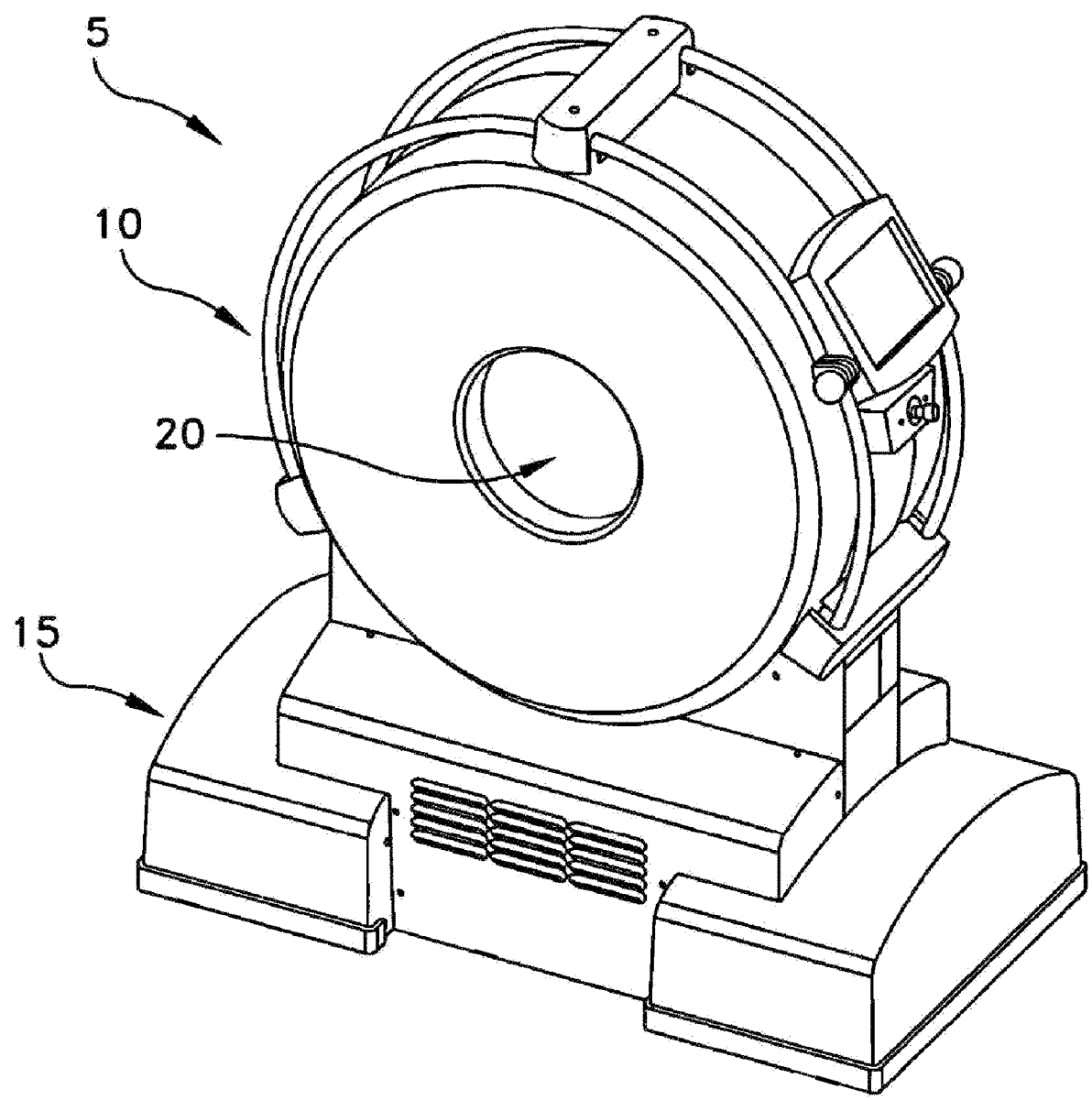
FIGS. 1 and 2 are schematic views showing the exterior of an exemplary CT imaging system.
Figure 2:
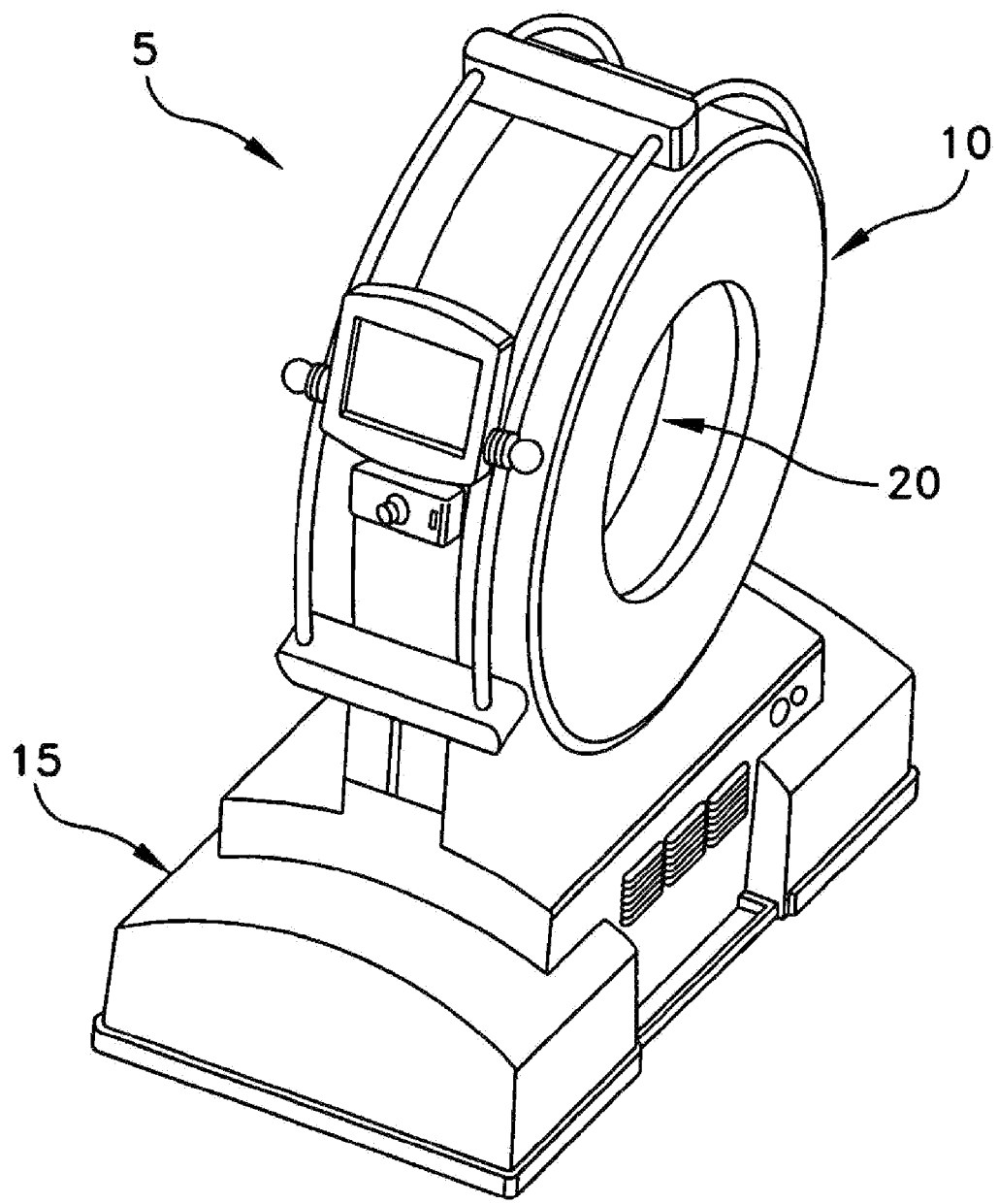
Figure 3:
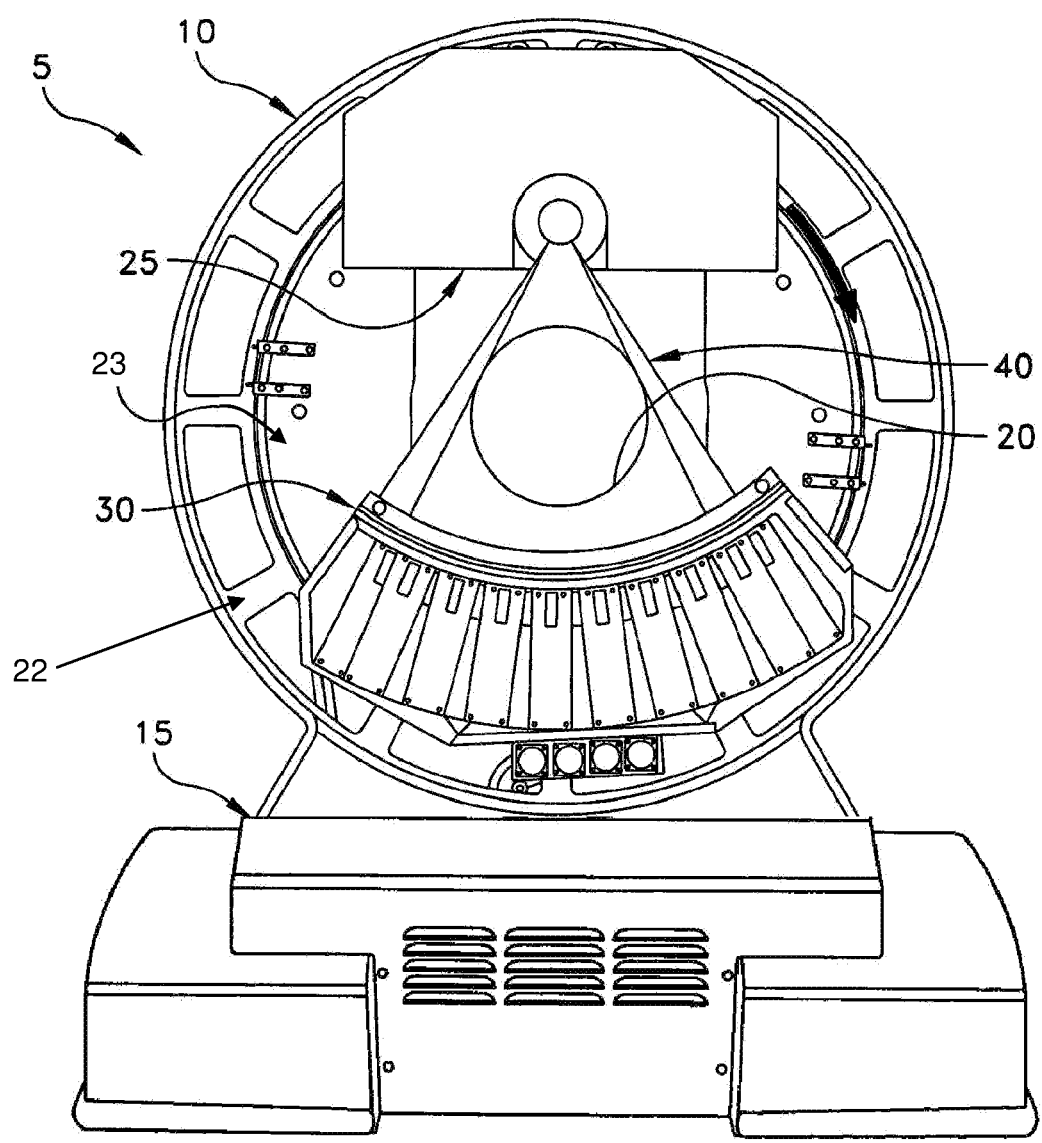
FIG. 3 is a schematic view showing various components in the torus of the exemplary CT imaging system shown in FIGS. 1 and 2.
Figure 4:
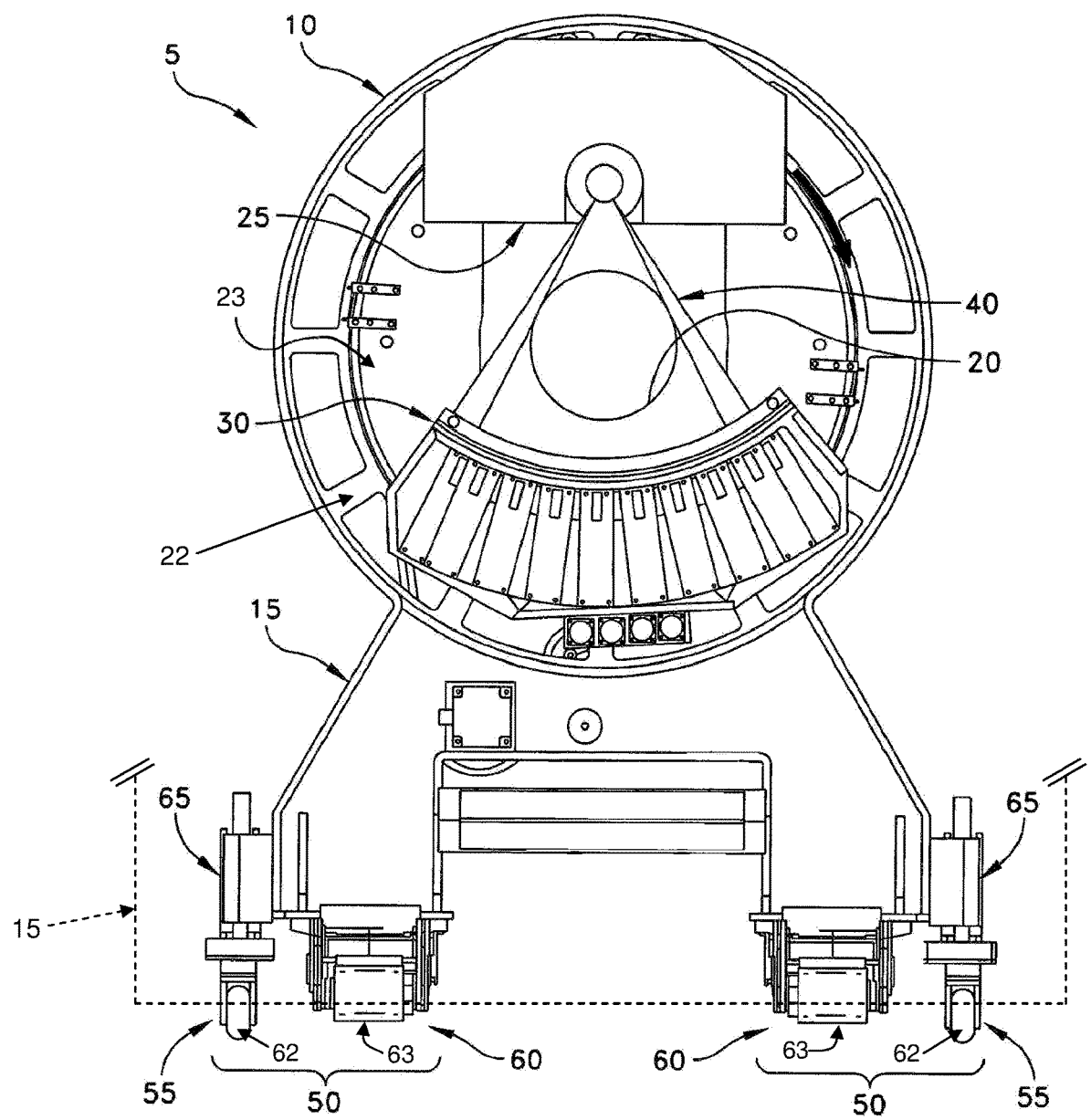
FIGS. 4 and 5 are schematic views showing an exemplary transport assembly for an exemplary mobile CT imaging system.
Figure 5:
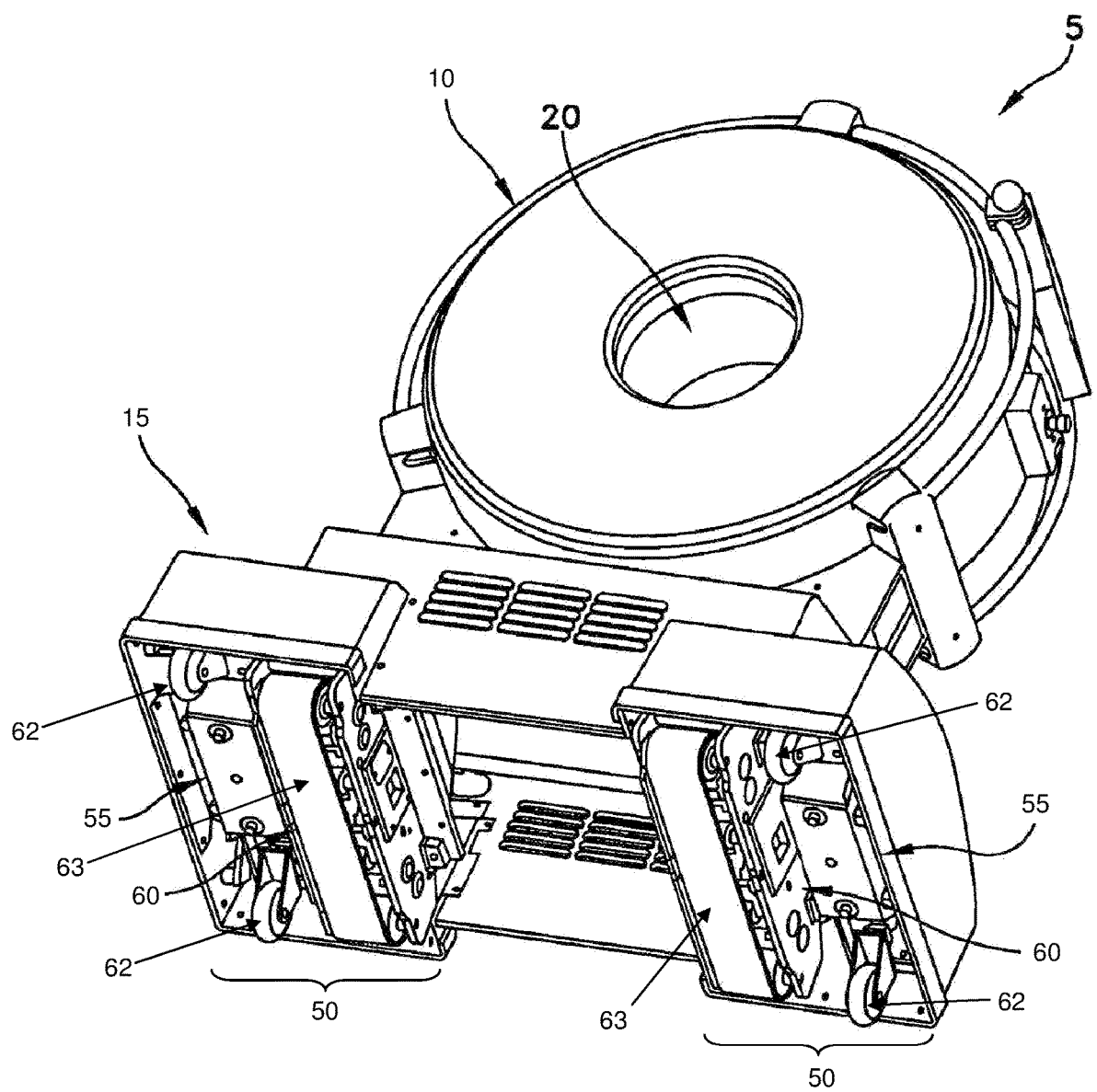
Figure 5B:
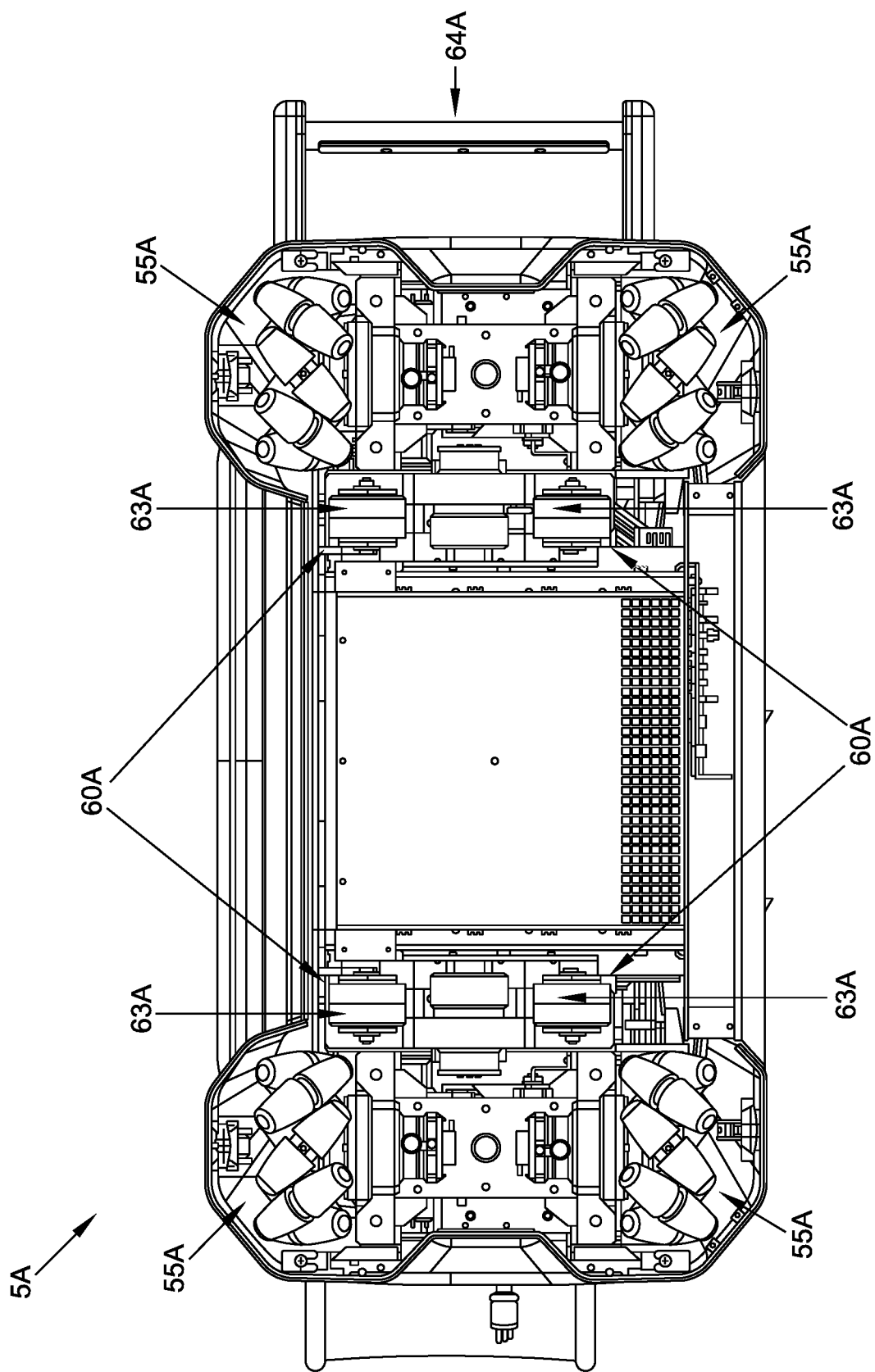
FIGS. 5A-5N are schematic views showing a novel mobile anatomical imaging system (e.g., a novel mobile CT imaging system) formed in accordance with the present invention, wherein the mobile CT imaging system comprises a gross movement mechanism in the form of an omnidirectional drive unit, and a fine movement mechanism in the form of powered wheels (also sometimes referred to herein as "motorized wheels")

More particularly, and looking now at FIGS. 5A and 5B, in one form of the invention, there is provided a mobile CT imaging system 5A which is substantially the same as the mobile CT imaging system 5 discussed above, except that (i) gross movement mechanism 55 of mobile CT imaging system 5 is replaced by gross movement mechanism 55A of mobile CT imaging system 5A, wherein gross movement mechanism 55A comprises a plurality of powered mecanum wheels 100 for providing mobile CT imaging system 5A with omnidirectional powered movement, and (ii) fine movement mechanism 60 of mobile CT imaging system 5 is replaced by fine movement mechanism 60A of mobile CT imaging system 5A, wherein fine movement mechanism 60A comprises a plurality of powered wheels 63A for moving of mobile CT imaging system 5A during scanning.

Figure 5C:
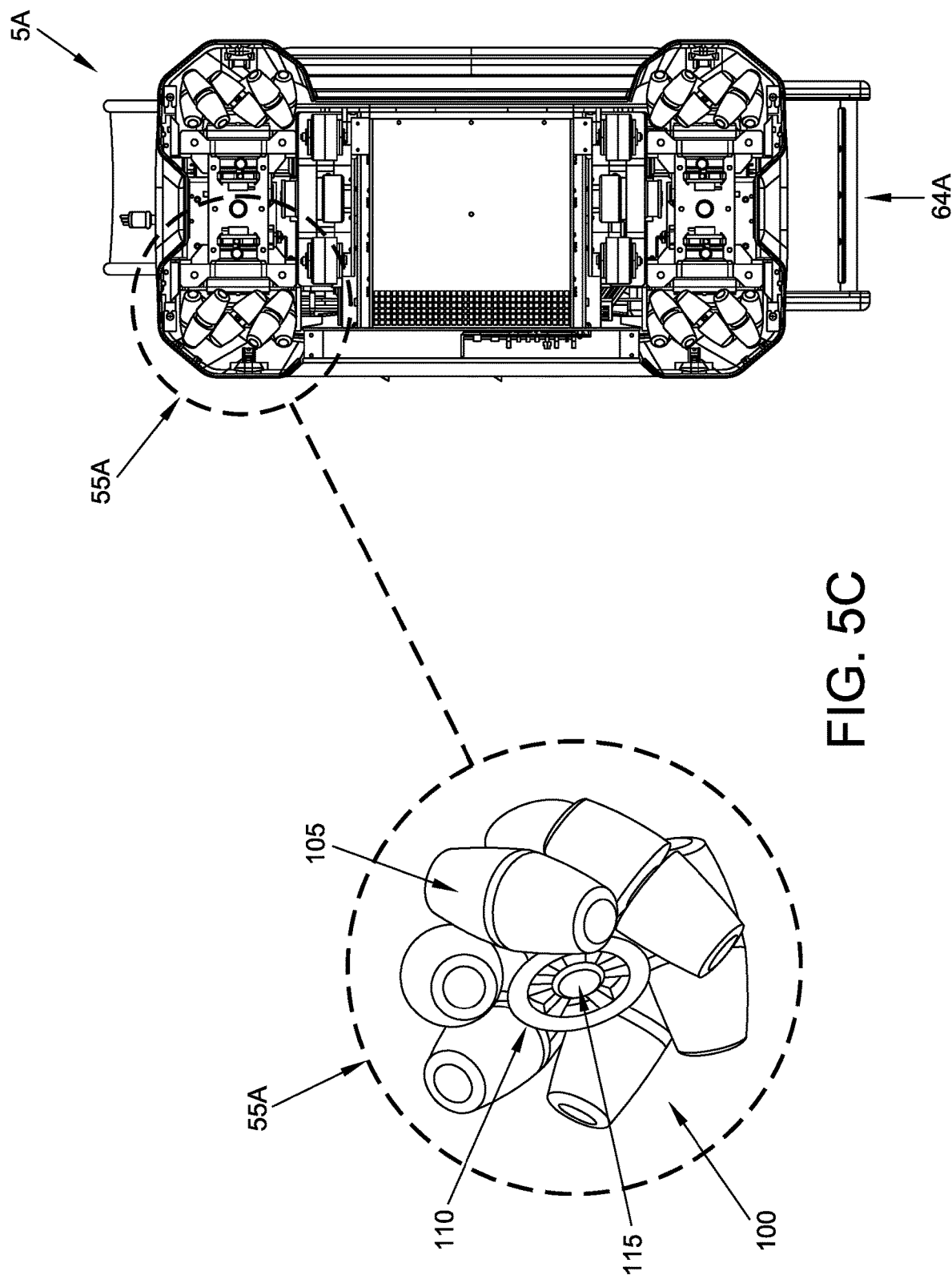
Figure 5D:
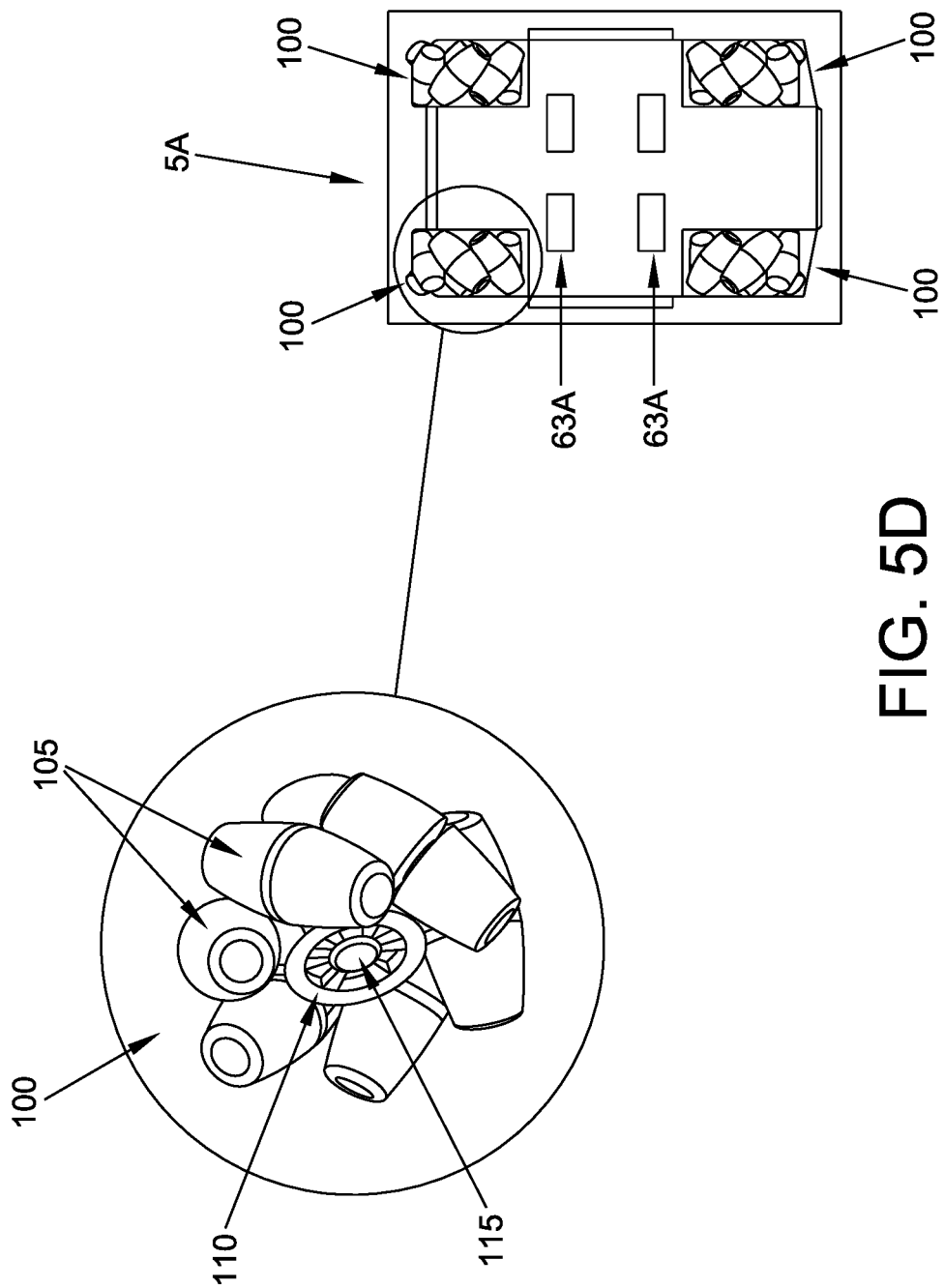

More particularly, and looking now at FIGS. 5C and 5D, in one form of the invention, gross movement mechanism 55A comprises a plurality of powered mecanum wheels 100 for selectively moving mobile CT imaging system 5A between scanning locations (mecanum wheels are also sometimes referred to as "omni wheels" or "ilon wheels"). Each mecanum wheel 100 comprises a plurality of rollers 105 arranged about a central hub 110, with each of the rollers 105 being oriented 45 degrees to the axis of rotation of hub 110. Each hub 110 is mounted to an axle 115 which is, in turn, mounted to a powered drive unit (e.g., a motor) within mobile CT imaging system 5A. As a result, each mecanum wheel 100 can be independently driven (i.e., rotated). As is well known in the art of mecanum wheels (and "omni wheels" or "ilon wheels"), by selectively driving (i.e., rotating) each of the mecanum wheels 100 in a coordinated fashion, omnidirectional powered movement of mobile CT imaging system 5A is enabled.

It should be appreciated that, for purposes of the present invention, the term "mecanum wheels" is intended to mean mecanum wheels, "omni wheels", "ilon wheels", and any other wheels of their type which, by selectively driving (i.e., rotating) individual ones of the wheels in a coordinated fashion with others of the wheels, enable omnidirectional powered movement of the mobile CT imaging system without requiring steering of individual wheels.

Figure 5E:
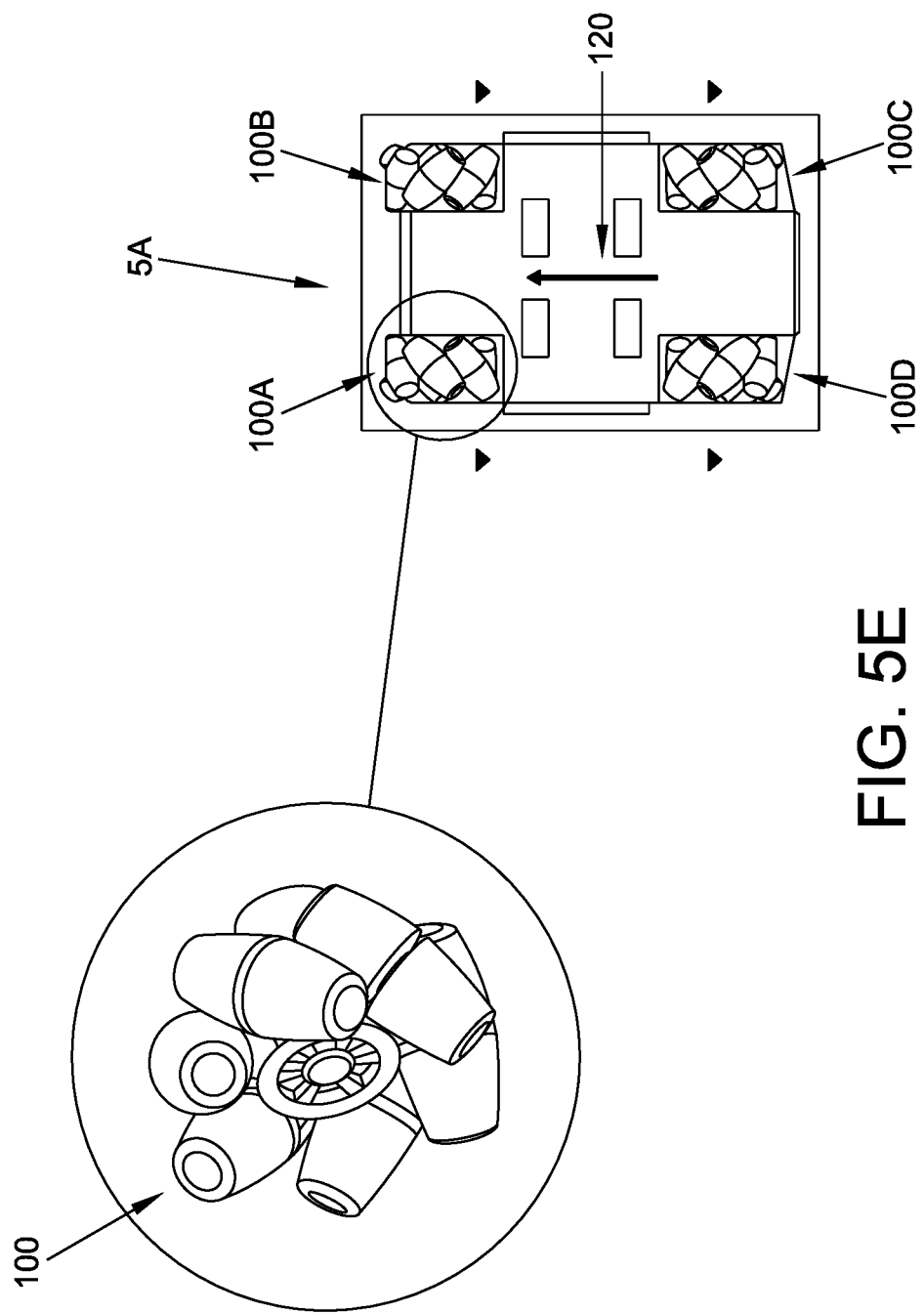

By way of example but not limitation, and looking now at FIG. 5E, when it is desired to move mobile CT imaging system 5A in the direction indicated by arrow 120, mecanum wheels 100A, 100B, 100C and 100D are all rotated in the same direction (i.e., in a direction opposite to the direction of arrow 120).

Figure 5F:
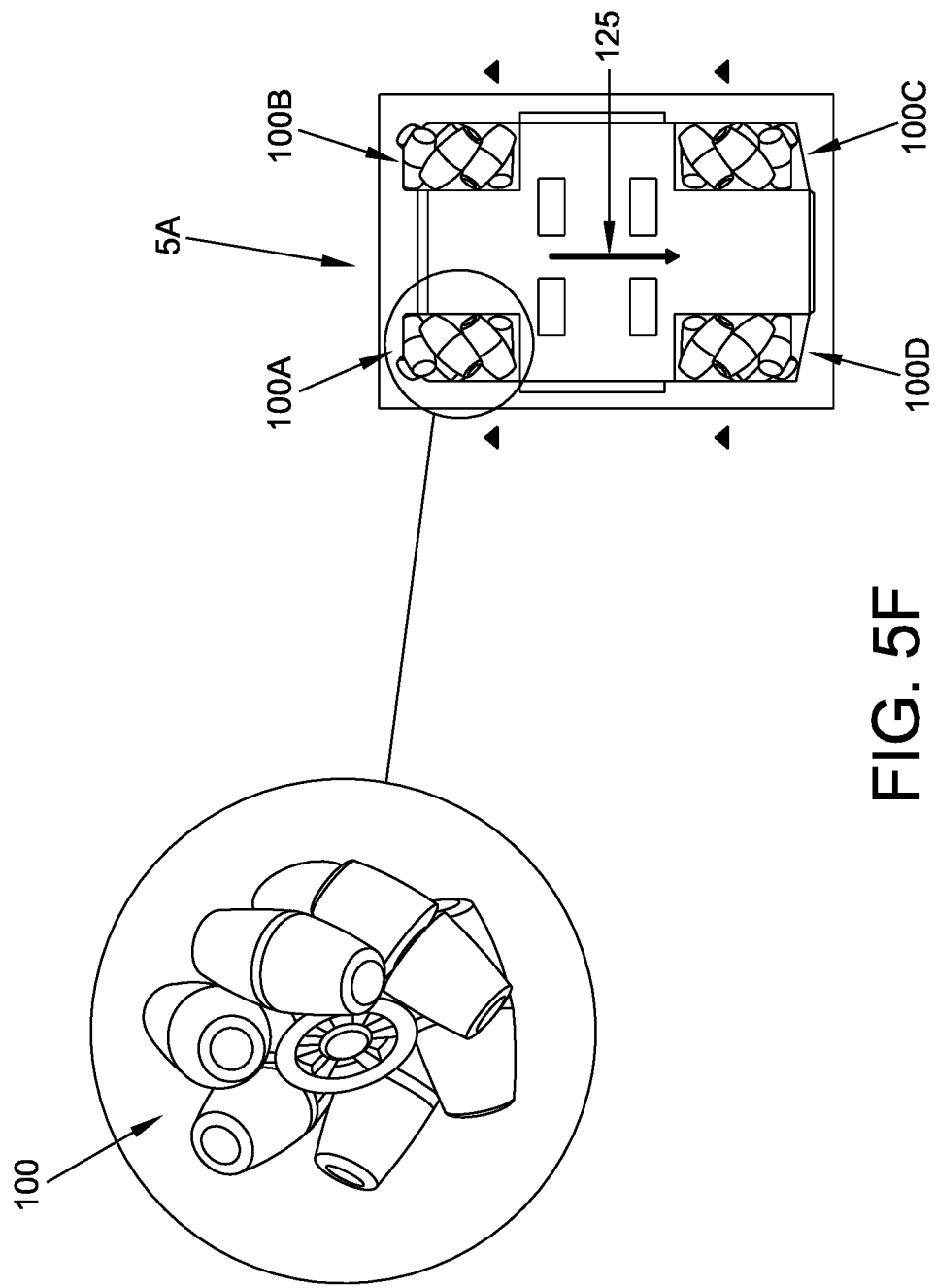

By way of further example but not limitation, and looking now at FIG. 5F, when it is desired to move mobile CT imaging system 5A in the direction indicated by arrow 125 (i.e., the direction opposite arrow 120 of FIG. 5E, but still in the direction of the long axis of mobile CT imaging system 5A), mecanum wheels 100A, 100B, 100C and 100D are all rotated in the same direction (i.e., in a direction opposite to the direction of arrow 125).

Figure 5G:
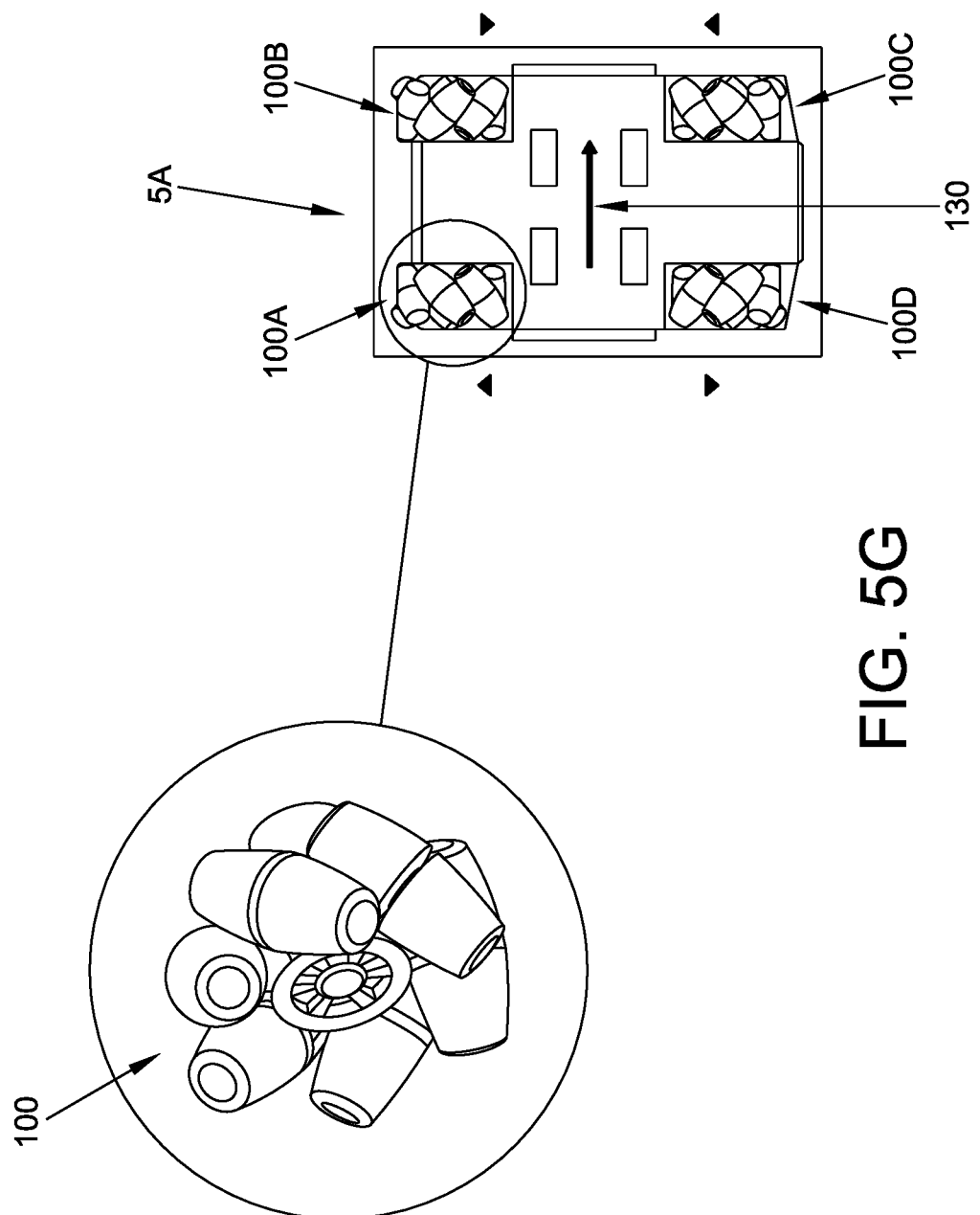

By way of still further example but not limitation, and looking now at FIG. 5G, when it is desired to move mobile CT imaging system 5A in the direction indicated by arrow 130 (i.e., in the direction of the short axis of mobile CT imaging system 5A), mecanum wheels 100A and 100C are moved in a first direction (i.e., perpendicular to the direction of arrow 130 and "up" according to the frame of reference of FIG. 5G) and mecanum wheels 100B and 100D are moved in a second, opposite direction (i.e., perpendicular to the direction of arrow 130 and "down" according to the frame of reference of FIG. 5G). It should be appreciated that due to the disposition of rollers 105 relative to central hub 110 of each of mecanum wheels 100A, 100B, 100C and 100D, the coordinated rotation of mecanum wheels 100A, 100B, 100C and 100D in this manner permits movement in a direction parallel to the longitudinal axes of axles 115 without requiring pivoting (i.e., "steering") of mecanum wheels 100A, 100B, 100C, 100D relative to mobile CT imaging system 5A.

Figure 5H:
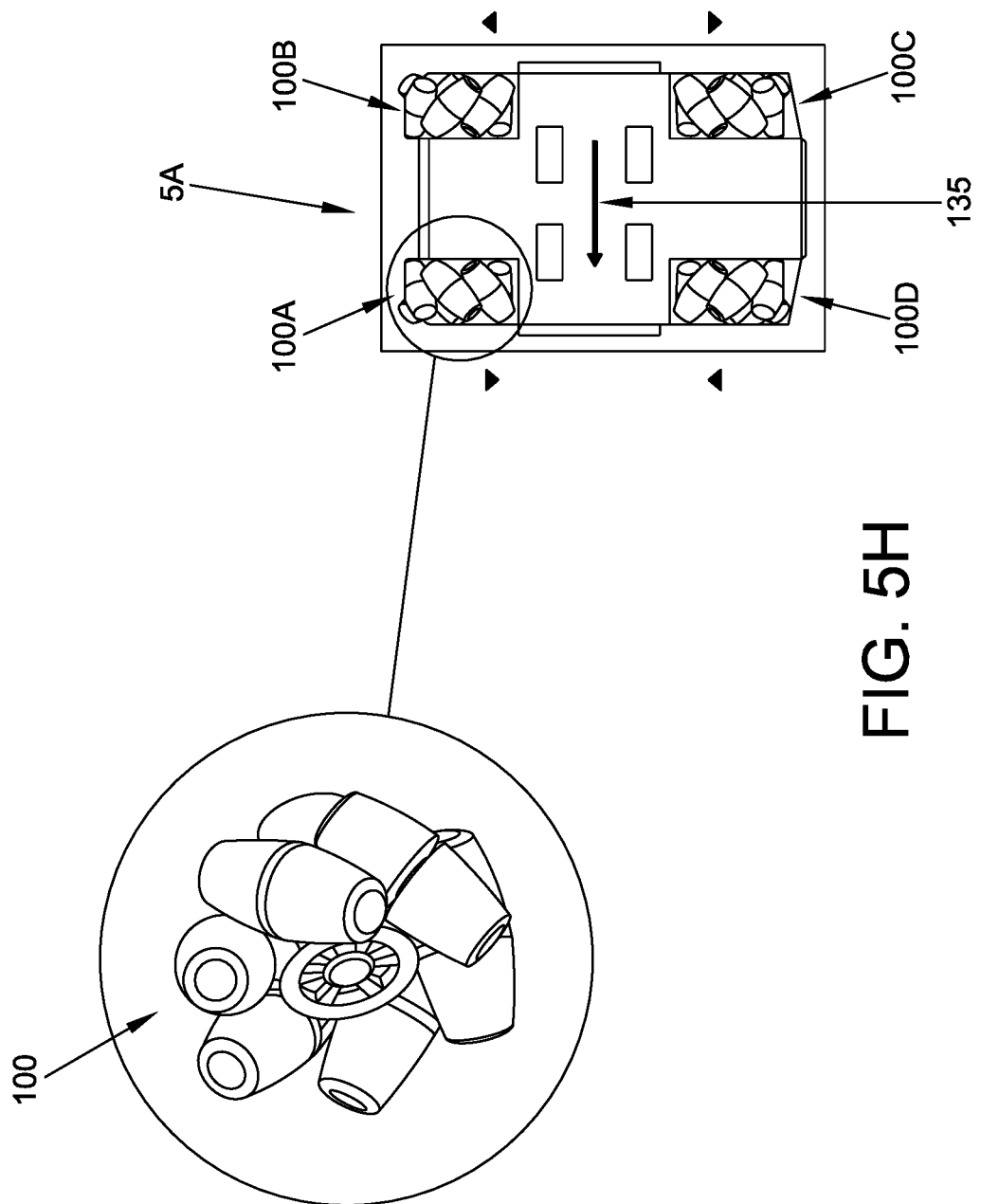

By way of still further example but not limitation, and looking now at FIG. 5H, when it is desired to move mobile CT imaging system 5A in the direction indicated by arrow 135 (i.e., the direction opposite arrow 130 of FIG. 5G, but still in the direction of the short axis of mobile CT imaging system 5A), mecanum wheels 100A and 100C are moved in a first direction (i.e., perpendicular to the direction of arrow 135 and "down" according to the frame of reference of FIG. 5H) and mecanum wheels 100B and 100D are moved in a second, opposite direction (i.e., perpendicular to the direction of arrow 135 and "up" according to the frame of reference of FIG. 5H). Again, as noted above, due to the disposition of rollers 105 relative to central hub 110 of each of mecanum wheels 100A, 100B, 100C and 100D, the coordinated rotation of mecanum wheels 100A, 100B, 100C and 100D in this manner permits movement in a direction parallel to the longitudinal axes of axles 115 without requiring pivoting (i.e., "steering") of mecanum wheels 100A, 100B, 100C, 100D relative to mobile CT imaging system 5A.

Figure 5I:
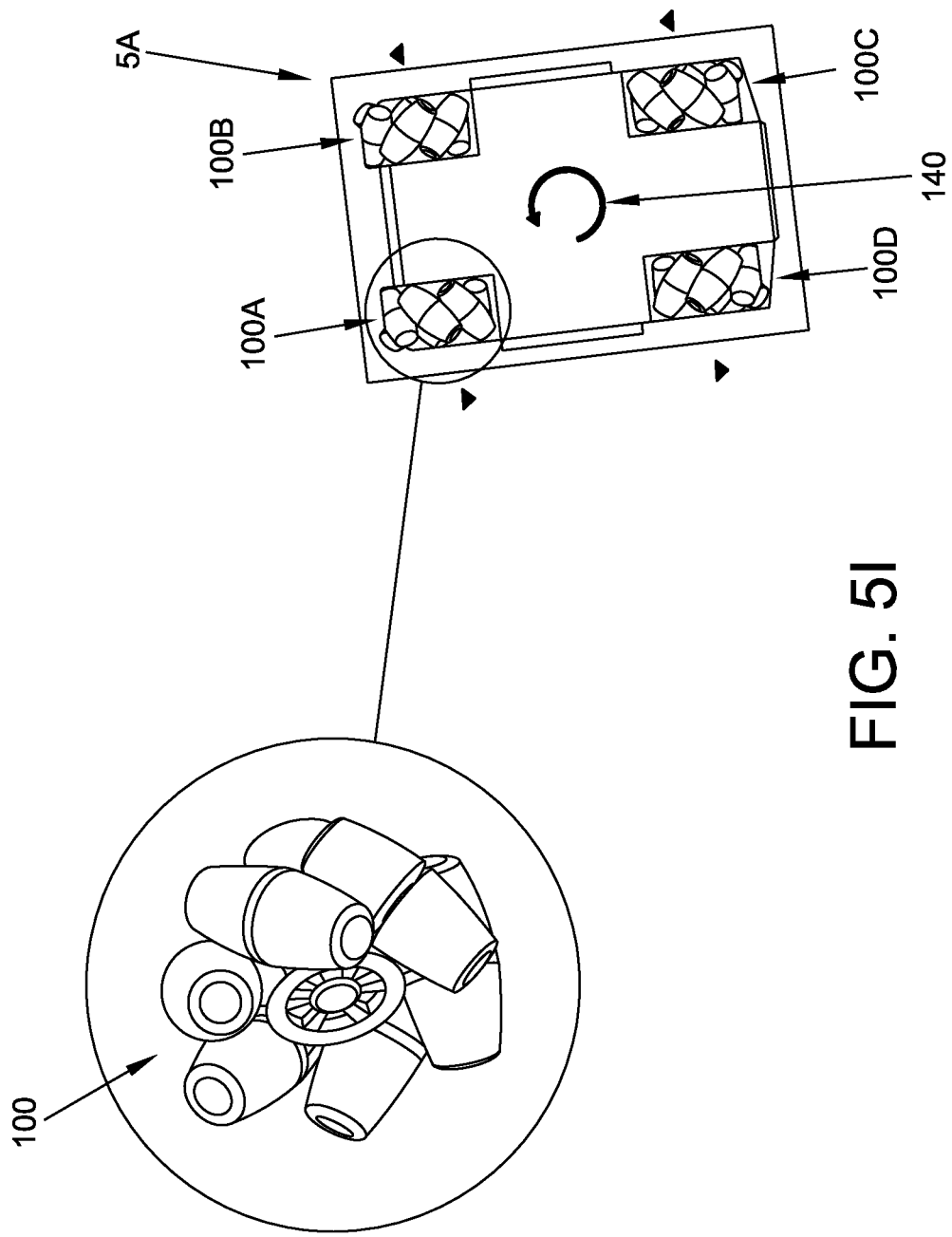

By way of further example but not limitation, and looking now at FIG. 5I, when it is desired to rotate mobile CT imaging system 5A in the direction indicated by arrow 140, mecanum wheels 100A and 100D are moved in a first direction (i.e., "down" according to the frame of reference of FIG. 5I) and mecanum wheels 100B and 100C are moved in a second, opposite direction (i.e., "up" according to the frame of reference of FIG. 5I). Again, as noted above, due to the disposition of rollers 105 relative to central hub 110 of each of mecanum wheels 100A, 100B, 100C and 100D, the coordinated rotation of mecanum wheels 100A, 100B, 100C and 100D in this manner permits rotation of mobile CT imaging system 5A without requiring pivoting (i.e., "steering") of mecanum wheels 100A, 100B, 100C, 100D relative to mobile CT imaging system 5A.

Figure 5J:
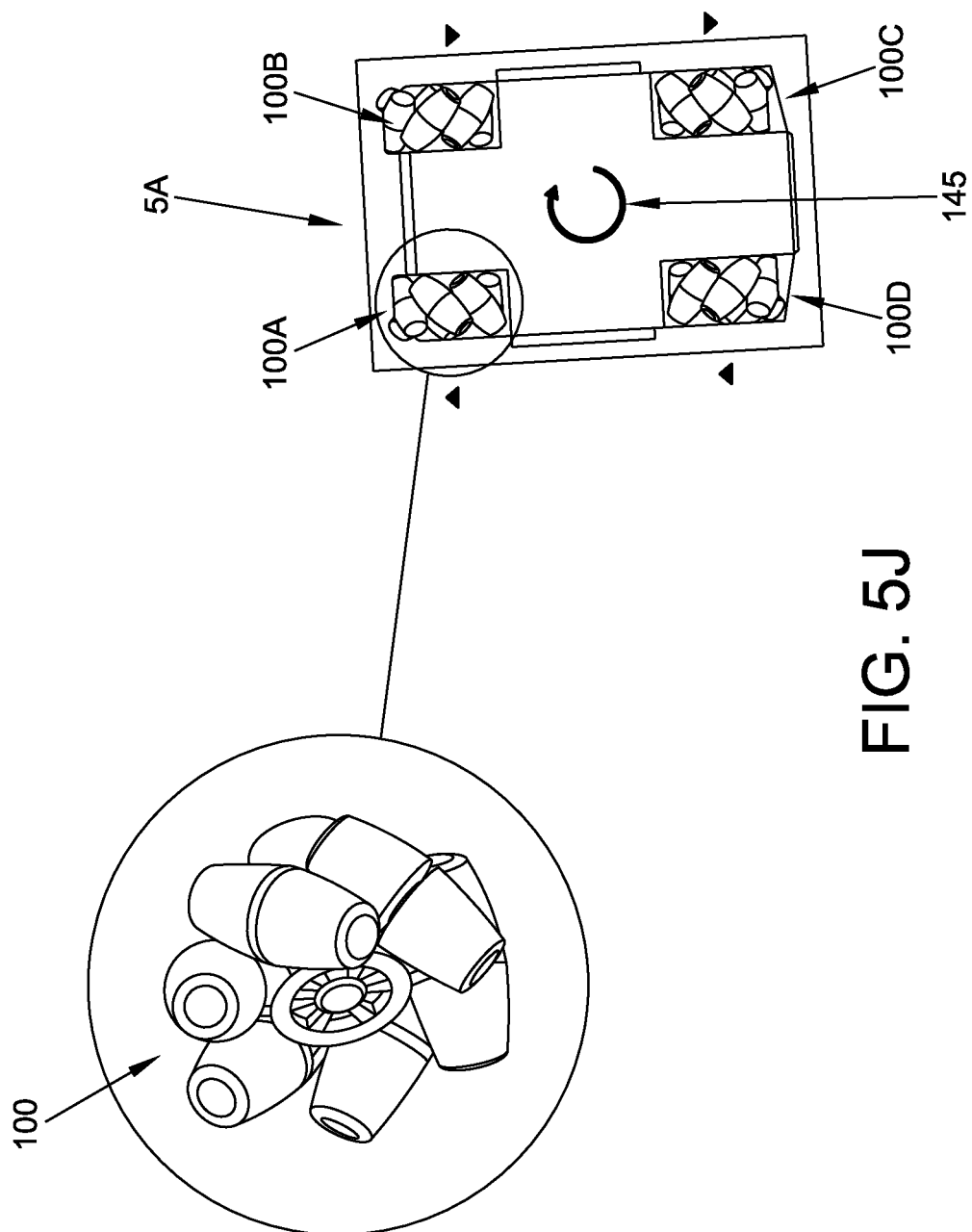
Figure 5K:
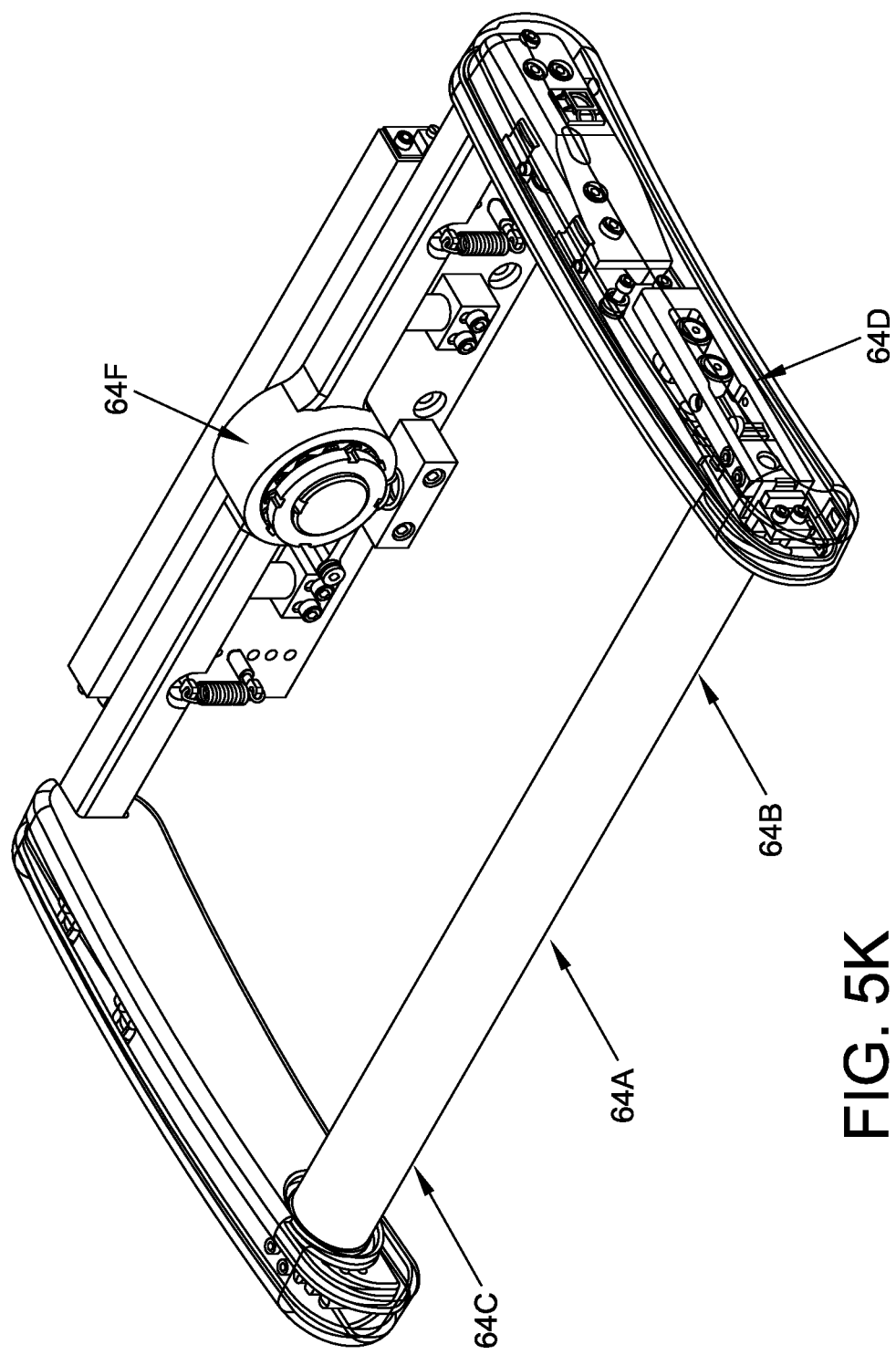

By way of still further example but not limitation, and looking now at FIG. 5J, when it is desired to rotate mobile CT imaging system 5A in the direction indicated by arrow 145, mecanum wheels 100A and 100D are moved in a first direction (i.e., "up" according to the frame of reference of FIG. 5J) and mecanum wheels 100B and 100C are moved in a second, opposite direction (i.e., "down" according to the frame of reference of FIG. 5J). Again, as noted above, due to the disposition of rollers 105 relative to central hub 110 of each of mecanum wheels 100A, 100B, 100C and 100D, the coordinated rotation of mecanum wheels 100A, 100B, 100C and 100D in this manner permits rotation of mobile CT imaging system 5A without requiring pivoting (i.e., "steering") of mecanum wheels 100A, 100B, 100C, 100D relative to mobile CT imaging system 5A.

It should be appreciated that the coordinated movements of mecanum wheels 100 (i.e., mecanum wheels 100A, 100B, 100C, 100D) discussed above are not intended to be limiting, and that other coordinated movements of mecanum wheels 100 are possible in order to achieve other desired movement of mobile CT imaging system 5A. By way of example but not limitation, certain mecanum wheels 100 may be rotated while others do not rotate, the relative speed of rotation of one or more of the mecanum wheels relative to others of the mecanum wheels may be varied, etc.

Thus, mecanum wheels 100 are essentially motorized wheels which, when operated in a coordinated fashion, can provide omnidirectional drive. Inasmuch as mecanum wheels 100 provide omnidirectional drive, the mecanum wheels allow mobile CT imaging system 5A to move in an infinitely-adjustable, omnidirectional manner. Significantly, the omnidirectional drive provided by mecanum wheels 100 enables mobile CT imaging system 5A to be moved over long distances (e.g., during transport of mobile CT imaging system 5A from one area of a hospital to another area of the hospital) and still permits extremely fine changes of the direction (and/or speed) of movement of mobile CT imaging system 5A, whereby to permit mobile CT imaging system 5A to be maneuvered around corners and corridors, around objects in rooms, etc.

Looking again at FIGS. 5A and 5B, fine movement mechanism 60A comprises a plurality of powered wheels 63A (also sometimes referred to herein as "motorized wheels") for moving mobile CT imaging system 5A during scanning. Powered wheels 63A are significantly less susceptible to floor irregularities than centipede belt drives 63. Thus, the use of powered wheels 63A during scanning can substantially eliminate lateral walk (or drift) over the complete stroke of a scan during scanning, even when the floor includes substantial irregularities, whereby to improve the accuracy of the scan results and avoid unintentional engagement of the CT imaging system with the bed or gurney which is supporting the patient.

In addition to the foregoing, each of the powered wheels 63A is independently driveable relative to every other powered wheel 63A. Thus, if mobile CT imaging system 5A begins to walk (or "drift") laterally during the course of scanning, the speed of rotation of one or more of the powered wheels 63A may be adjusted so as to re-align mobile CT imaging system 5A with the scan path (i.e., with the bed or gurney which is supporting the patient).

Thus, with mobile CT imaging system 5A, the mobile CT imaging system may be pre-positioned in an "out of the way" location (e.g., in an unused corner of an emergency room) and then, when a patient requires scanning, the patient may be quickly and easily scanned at their bedside, by simply moving the mobile CT imaging system to the patient's bedside on gross movement mechanism 55A (e.g., mecanum wheels 100), and thereafter moving the mobile CT imaging system during scanning on fine movement mechanism 60A (e.g., on powered wheels 63A).

In one preferred form of the invention, and looking now at FIGS. 5A-5C, 5K and 5L, a drive bar 64A is provided to control the application of power to each of the mecanum wheels 100. Drive bar 64A comprises a right side 64B and a left side 64C. Preferably, drive bar 64A is configured so that:

(i) when the right side 64B of drive bar 64A and the left side 64C of drive bar 64A are both pressed forwardly (i.e., toward the body of the mobile CT imaging system 5A), mecanum wheels 100 are caused to move mobile CT imaging system 5A forwardly, e.g., in the manner of FIG. 5E;

(ii) when the right side 64B of drive bar 64A and the left side 64C of drive bar 64A are both pulled rearwardly (i.e., away from the body of the mobile CT imaging system 5A), mecanum wheels 100 are caused to move mobile CT imaging system 5A rearwardly, e.g., in the manner of FIG. 5F;

(iii) when the right side 64B of drive bar 64A is pressed forwardly and the left side 64C of drive bar 64A is pulled rearwardly, mecanum wheels 100 are caused to rotate mobile CT imaging system 5A to the left, e.g., in the manner of FIG. 5I;

(iv) when the right side 64B of drive bar 64A is pulled rearwardly and the left side 64C of drive bar 64A is pushed forwardly, mecanum wheels 100 are caused to rotate mobile CT imaging system 5A to the right, e.g., in the manner of FIG. 5J;

(v) when the right side 64B of drive bar 64A is lifted upwardly and the left side 64C of drive bar 64A is pushed downwardly, mecanum wheels 100 are caused to move mobile CT imaging system 5A laterally to the left, e.g., in the manner of FIG. 5H; and (vi) when the right side 64B of drive bar 64A is pushed downwardly and the left side 64C of drive bar 64A is pulled upwardly, mecanum wheels 100 are caused to move mobile CT imaging system 5A laterally to the right, e.g., in the manner of FIG. 5G.

In one preferred form of the invention, a forward/backward sensing element 64D is used to sense forward/backward movement of the right side 64B of drive bar 64A, a forward/backward sensing element 64E is used to sense forward/backward movement of the left side 64C of drive bar 64A, and a "strafe" sensing element 64F is used to sense upward/downward movements of the right side 64B of drive bar 64A and the left side 64C of drive bar 64A. In one preferred form of the invention, forward/backward sensing element 64D comprises four sensors (e.g., strain gauges) for sensing forward/backward movement of the right side 64B of drive bar 64A, forward/backward sensing element 64E comprises four sensors (e.g., strain gauges) for sensing forward/backward movement of the left side 64C of drive bar 64A, and "strafe" sensing element 64F comprises two sensors (e.g., strain elements) for sensing upward/downward movements of the right side 64B of drive bar 64A and the left side 64C of drive bar 64A.

Figure 5M:
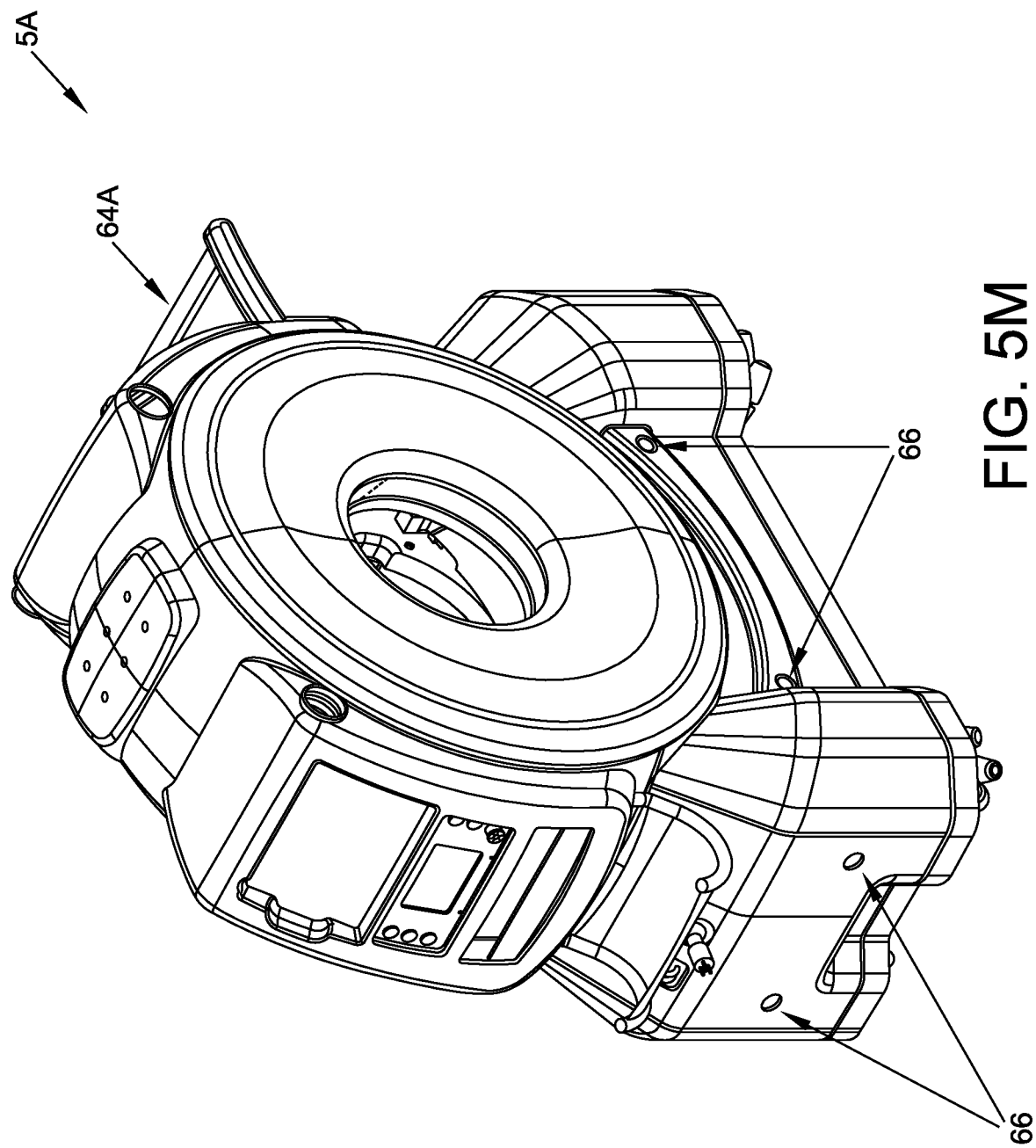
Figure 5N:
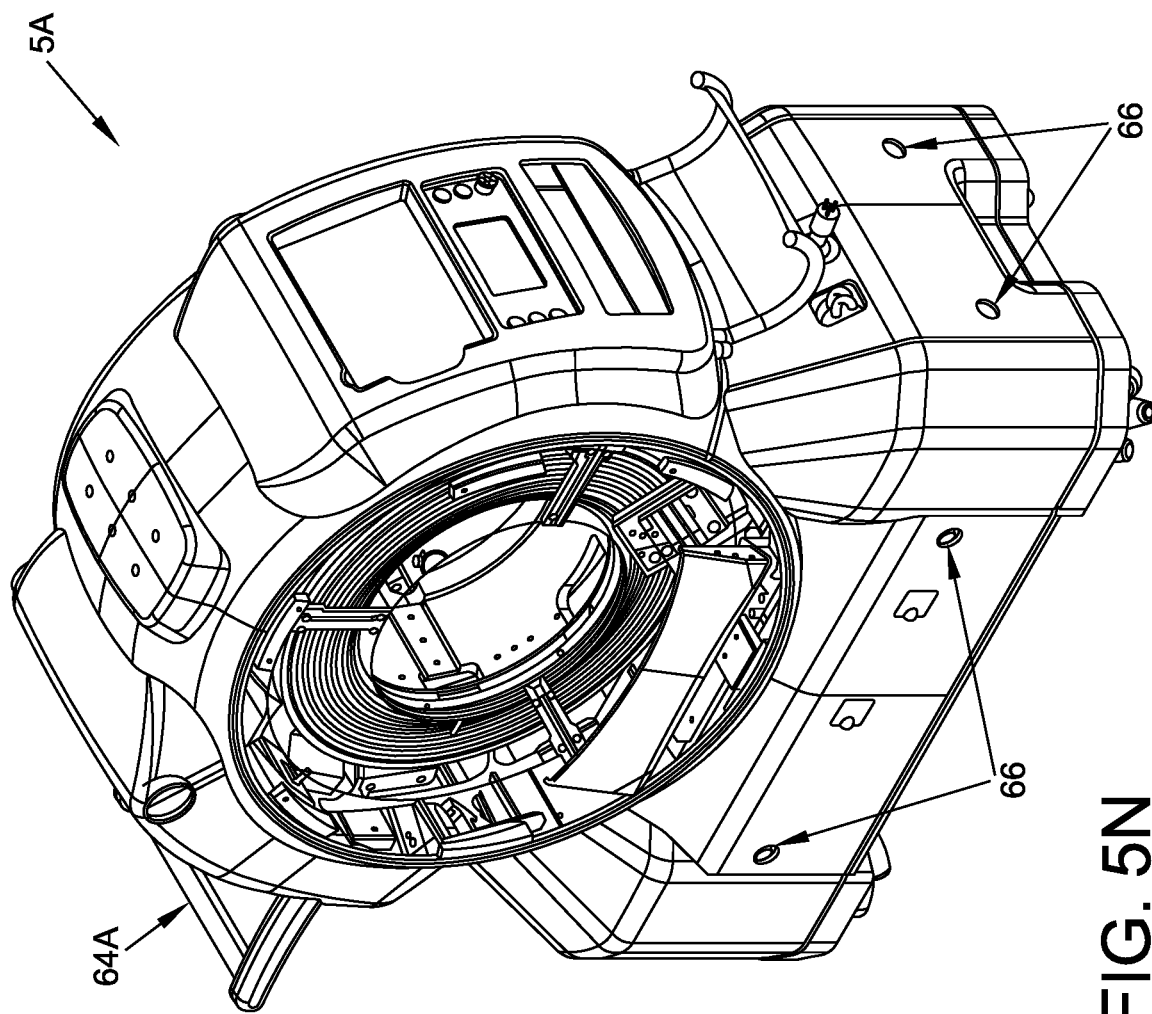

In one preferred form of the invention, and looking now at FIGS. 5M and 5N, mobile CT imaging system 5A comprises a collision sensor system utilizing six ultrasound sensors 66 for sensing the proximity of mobile CT imaging system 5A to adjacent objects (e.g., walls, corners, people, equipment, beds, gurneys, etc.). The collision sensor system is configured to warn an operator of obstacles in the drive path of mobile CT imaging system 5A or obstacles to the sides of mobile CT imaging system 5A. When an obstacle is detected in close proximity to mobile CT imaging system 5A, an audible alarm can be sounded. In addition, the collision sensor system can also be configured to automatically decrease the speed of the mobile CT imaging system 5A as a function of (i) the speed of the mobile CT imaging system 5A, and (ii) the distance of the mobile CT imaging system 5A from the object.

It should also be appreciated that, if desired, gross movement mechanism 55A may utilize steerable powered castors (also sometimes referred to herein as "steerable motorized castors") in place of mecanum wheels 100. In this case, individual ones of the steerable powered castors rotate about a pivot so as to provide steering for the powered castors.

Novel Mobile CT Imaging System Utilizing A
Novel Omnidirectional Powered Drive Unit
Comprising Steerable Powered Castors In accordance with the present invention, there is also provided a new and improved anatomical imaging system (e.g., a mobile CT imaging system) which includes a new and improved omnidirectional powered drive unit for the anatomical imaging system which can substantially eliminate lateral walk (or drift) over the complete stroke of the scan, even when the floor includes substantial irregularities, whereby to improve the accuracy of the scan results and avoid unintentional engagement of the anatomical imaging system with the bed or gurney which is supporting the patient. In accordance with the present invention, the omnidirectional powered drive unit comprises a plurality of independently drivable, independently steerable motorized castors which serve as both (i) the gross movement mechanism for moving the mobile CT machine over long distances, and (ii) the fine movement mechanism for moving the mobile CT machine during scanning, as will hereinafter be discussed in further detail.

Figure 6:
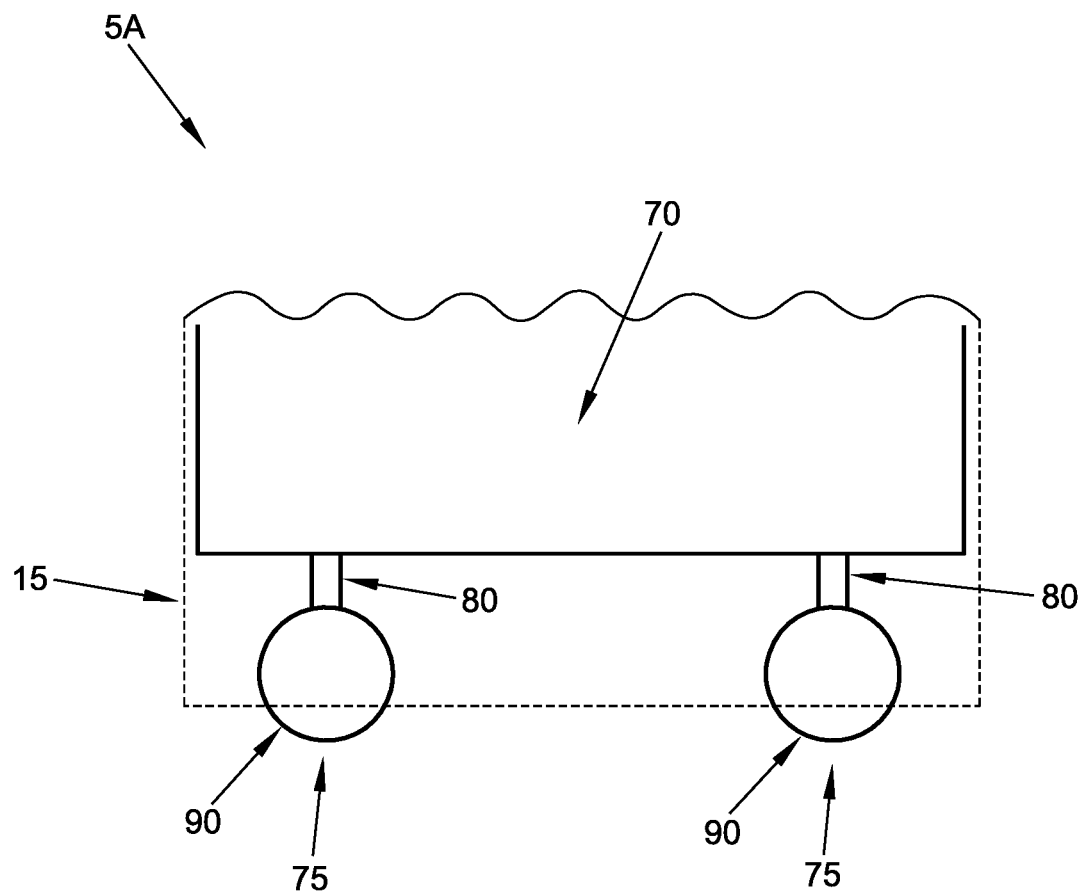
FIG. 6 is a schematic side view showing a novel anatomical imaging system (e.g., a novel mobile CT imaging system) formed in accordance with the present invention, wherein the novel mobile CT imaging system comprises a novel omnidirectional powered drive unit comprising a plurality of steerable motorized castors (also sometimes referred to herein as "steerable powered castors")
Figure 7:
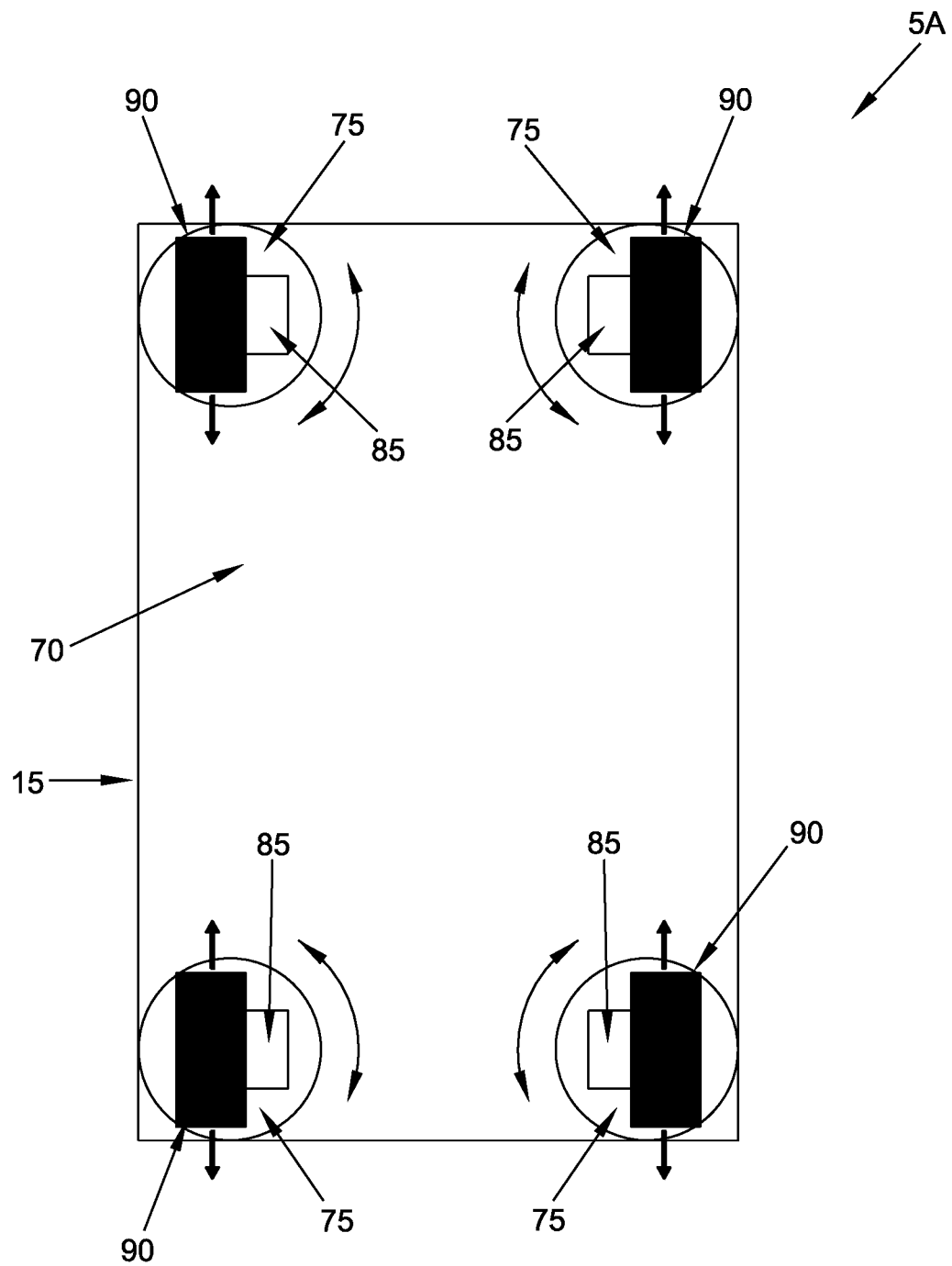
FIG. 7 is a schematic bottom view showing the bottom of the novel mobile CT imaging system shown in FIG. 6, wherein the novel mobile CT imaging system comprises a novel omnidirectional powered drive unit comprising a plurality of steerable motorized castors.

More particularly, and looking now at FIGS. 6 and 7, in one form of the invention, there is provided a mobile CT imaging system 5A wherein base 15 of the mobile CT imaging system comprises an omnidirectional powered drive unit 70 comprising a plurality of independently drivable, independently steerable motorized castors 75 (also sometimes referred to herein as "powered castors") for selectively moving mobile CT imaging system 5A (e.g., over long distances to be brought to the patient and over short distances during scanning of the patient). Each motorized castor 75 is mounted to a post 80 (FIG. 6) which extends downward from omnidirectional powered drive unit 70. Steerable motorized castors 75 are configured to rotate about posts 80 so as to steer the motorized castors, and each of the steerable motorized castors is configured to be independently driven. Thus, each motorized castor 75 is independently drivable and independently steerable.

By selectively driving and steering each of the motorized castors 75 in a coordinated fashion, omnidirectional powered drive unit 70 enables omnidirectional powered movement of mobile CT imaging system 5A, as will hereinafter be discussed in further detail. Put another way, steerable motorized castors 75 essentially comprise motorized wheels which can be independently rotated about the posts 80 and independently driven (e.g., via a drive motor 85 provided for each of the wheels 90). Inasmuch as steerable motorized castors 75 are independently rotatable about their posts 80, and independently drivable, steerable motorized castors 75 allow mobile CT imaging system 5A to move in an infinitely-adjustable, omnidirectional manner, whereby to compensate for any lateral walk (or drift) which may occur during the course of a scan due to floor tilt.

By way of example but not limitation, if mobile CT imaging system 5A begins to walk (or "drift") laterally during the course of scanning, the direction and/or speed of rotation of one or more of the steerable motorized castors 75 may be adjusted so as to re-align mobile CT imaging system 5A with the scan path (i.e., with the bed or gurney which is supporting the patient).

It should be appreciated that the provision of an omnidirectional powered drive unit 70 comprising a plurality of independently drivable, independently steerable motorized castors 75 allows for a wide range of movement for mobile CT imaging system 5A, over both long distances (e.g., during transport of mobile CT imaging system 5A from one area of a hospital to another area of the hospital) and short distances (e.g., during scanning). At the same time, omnidirectional powered drive unit 70 permits extremely fine adjustment of the direction (and/or speed) of movement of mobile CT imaging system 5A, whereby to permit real-time re-alignment of mobile CT imaging system 5A with a scan path during scanning.

Use Of Omnidirectional Powered Drive Unit 70

In accordance with the present invention, ominidirectional powered drive unit 70 can be used to move mobile CT imaging system 5A as follows. Initially, mobile CT imaging system 5A is maneuvered about a room using its independently drivable, independently steerable motorized castors 75 so that mobile CT imaging system 5A is properly aligned with the patient who is to be scanned, i.e., with the bed or gurney upon which the patient is lying. Thereafter, when scanning is to be commenced, ominidirectional powered drive unit 70 uses its independently drivable, independently steerable motorized castors 75 to move mobile CT imaging system 5A precisely relative to the patient during scanning.

More particularly, during scanning, steerable motorized castors 75 are driven so as to move mobile CT imaging system 5A along the scan path. If mobile CT imaging system 5A begins to deviate from the scan path during the course of scanning (e.g., due to imperfections in the floor over which steerable motorized castors 75 move), one or more of the steerable motorized castors 75 can be selectively rotated about their posts 80, and/or the speed of one or more of the steerable motorized castors 75 can be adjusted, so as to re-align mobile CT imaging system 5A with the scan path. It should be appreciated that such adjustments may be effected in real-time so as to dynamically adjust the movement of mobile CT imaging system 5A during scanning. As a result, mobile CT imaging system 5A can better track the scan path during scanning.

Novel CT Imaging System Utilizing A Novel Omnidirectional Powered Drive Unit Comprising Mecanum Wheels In another form of the present invention, there is provided another new and improved anatomical imaging system (e.g., a mobile CT imaging system) which includes a new and improved omnidirectional powered drive unit for the anatomical imaging system which can substantially eliminate lateral walk (or drift) over the complete stroke of the scan, even when the floor includes substantial irregularities, whereby to improve the accuracy of the scan results and avoid unintentional engagement of the anatomical imaging system with the bed or gurney which is supporting the patient. In accordance with the present invention, the omnidirectional powered drive unit comprises a plurality of independently drivable mecanum wheels which serve as both (i) the gross movement mechanism for moving the CT machine over long distances, and (ii) the fine movement mechanism for moving the mobile CT machine during scanning, as will hereinafter be discussed in further detail.

Figure 8:
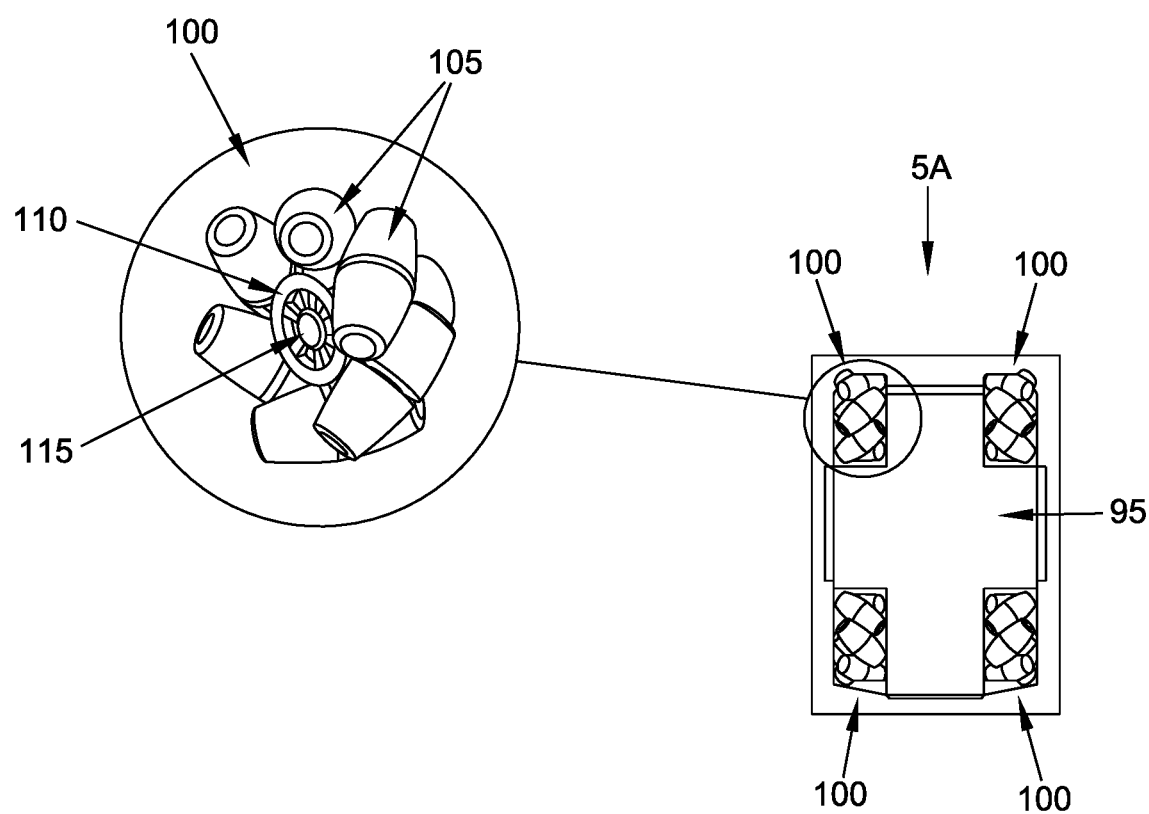
FIG. 8 is a schematic bottom view showing a novel anatomical imaging system (e.g., a novel mobile CT imaging system) formed in accordance with the present invention, wherein the novel mobile CT imaging system comprises a novel omnidirectional powered drive unit comprising a plurality of mecanum wheels.

More particularly, and looking now at FIG. 8, in one form of the invention, base 15 of mobile CT imaging system 5A comprises an omnidirectional powered drive unit 95 comprising a plurality of mecanum wheels 100 for selectively moving mobile CT imaging system 5A (mecanum wheels are also sometimes referred to as "omni wheels" or "ilon wheels"). Each mecanum wheel 100 comprises a plurality of rollers 105 arranged about a central hub 110, with each of the rollers 105 being oriented 45 degrees to the axis of rotation of hub 110. Each hub 110 is mounted to an axle 115 which is, in turn, mounted to omnidirectional powered drive unit 95. As a result, each mecanum wheel 100 can be independently driven, whereby to permit mobile CT imaging system 5A to be moved in any direction (e.g., over long distances to be brought to the patient and over short distances during scanning of the patient), as will hereinafter be discussed in further detail. By selectively driving each of the mecanum wheels 100 in a coordinated fashion, omnidirectional powered drive unit 95 enables omnidirectional powered movement of mobile CT imaging system 5A, as will hereinafter be discussed in further detail.

Figure 9:
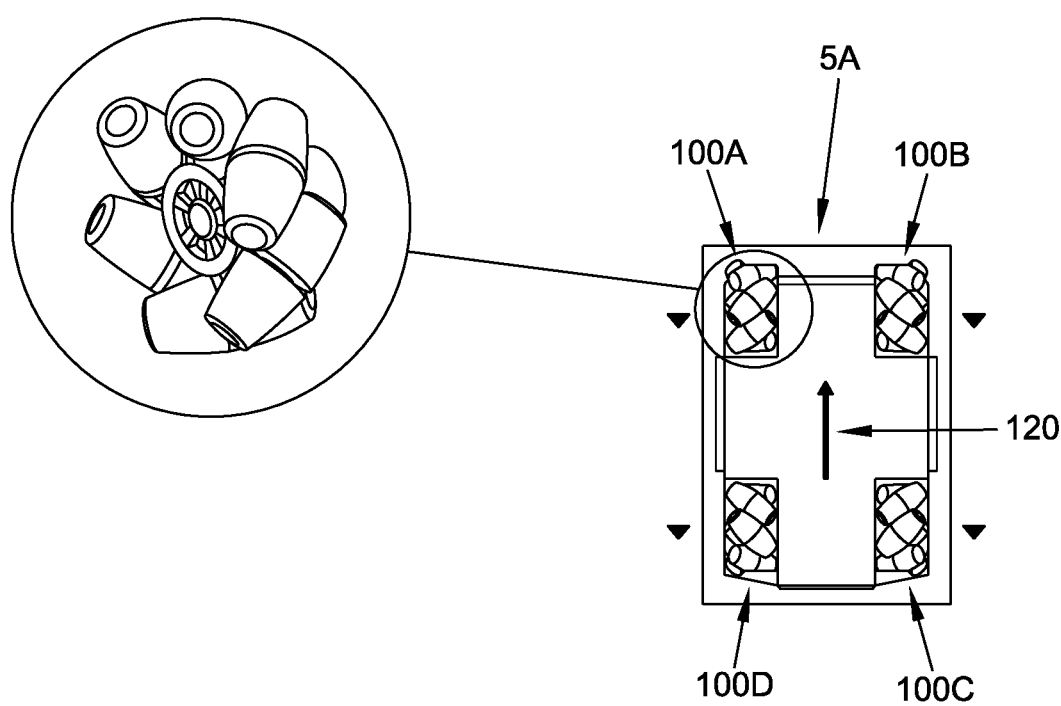
FIGS. 9-14 are schematic bottom views showing how the novel anatomical imaging system (e.g., the novel mobile CT imaging system) of FIG. 8 can be moved in various directions by selectively rotating a plurality of the mecanum wheels of the novel omnidirectional powered drive unit of FIG. 8.

By way of example but not limitation, and looking now at FIG. 9, when it is desired to move mobile CT imaging system 5A in the direction indicated by arrow 120 (i.e., in the direction of the long axis of mobile CT imaging system 5A, such as may be the case when moving mobile CT imaging system 5A over long distances), mecanum wheels 100A, 100B, 100C and 100D are all rotated in the same direction (i.e., in a direction opposite to the direction of arrow 120, taken from the frame of reference of FIG. 9).

Figure 10:
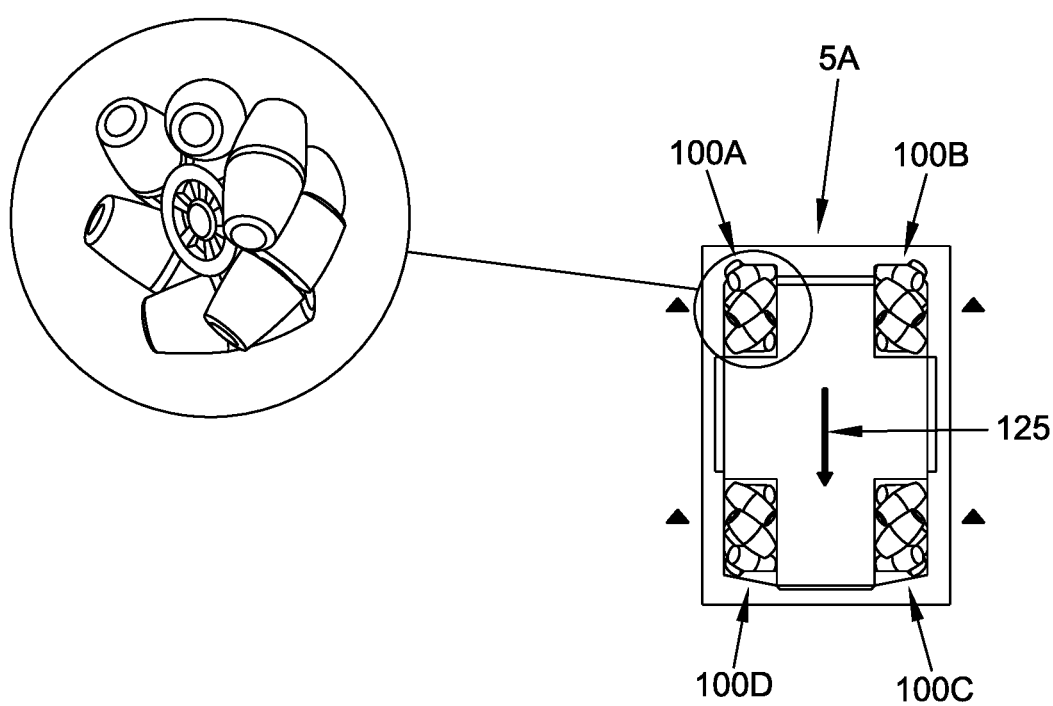

By way of further example but not limitation, and looking now at FIG. 10, when it is desired to move mobile CT imaging system 5A in the direction indicated by arrow 125 (i.e., the direction opposite arrow 120 of FIG. 9, but still in the direction of the long axis of mobile CT imaging system 5A, such as may be the case when moving mobile CT imaging system 5A over long distances), mecanum wheels 100A, 100B, 100C and 100D are all rotated in the same direction (i.e., in a direction opposite to the direction of arrow 125, taken from the frame of reference of FIG. 10).

Figure 11:
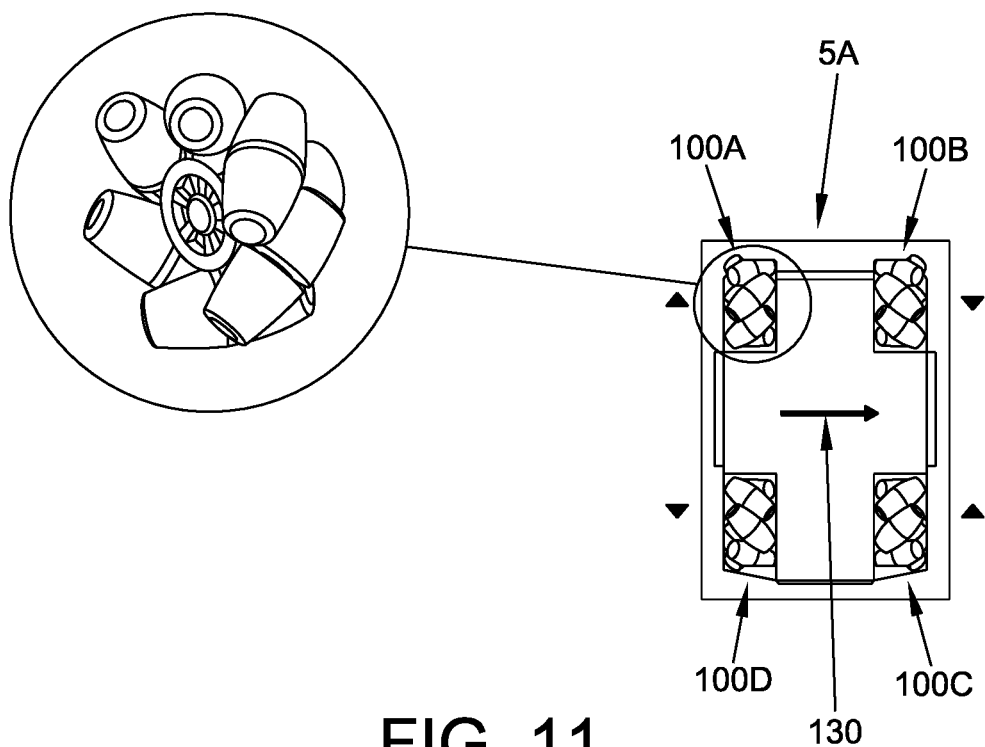

By way of still further example but not limitation, and looking now at FIG. 11, when it is desired to move mobile CT imaging system 5A in the direction indicated by arrow 130 (i.e., in the direction of the short axis of mobile CT imaging system 5A, such as may be the case when moving mobile CT imaging system 5A during scanning), mecanum wheels 100A and 100C are moved in a first direction (i.e., perpendicular to the direction of arrow 130 and "up" according to the frame of reference of FIG. 11) and mecanum wheels 100B and 100D are moved in a second, opposite direction (i.e., perpendicular to the direction of arrow 130 and "down" according to the frame of reference of FIG. 11). It should be appreciated that due to the disposition of rollers 105 relative to central hub 110 of each of mecanum wheels 100A, 100B, 100C and 100D, the coordinated rotation of mecanum wheels 100A, 100B, 100C and 100D in this manner permits movement in a direction parallel to the longitudinal axes of axles 115 without requiring pivoting (i.e., "steering") of mecanum wheels 100A, 100B, 100C, 100D relative to omnidirectional powered drive unit 95.

Figure 12:
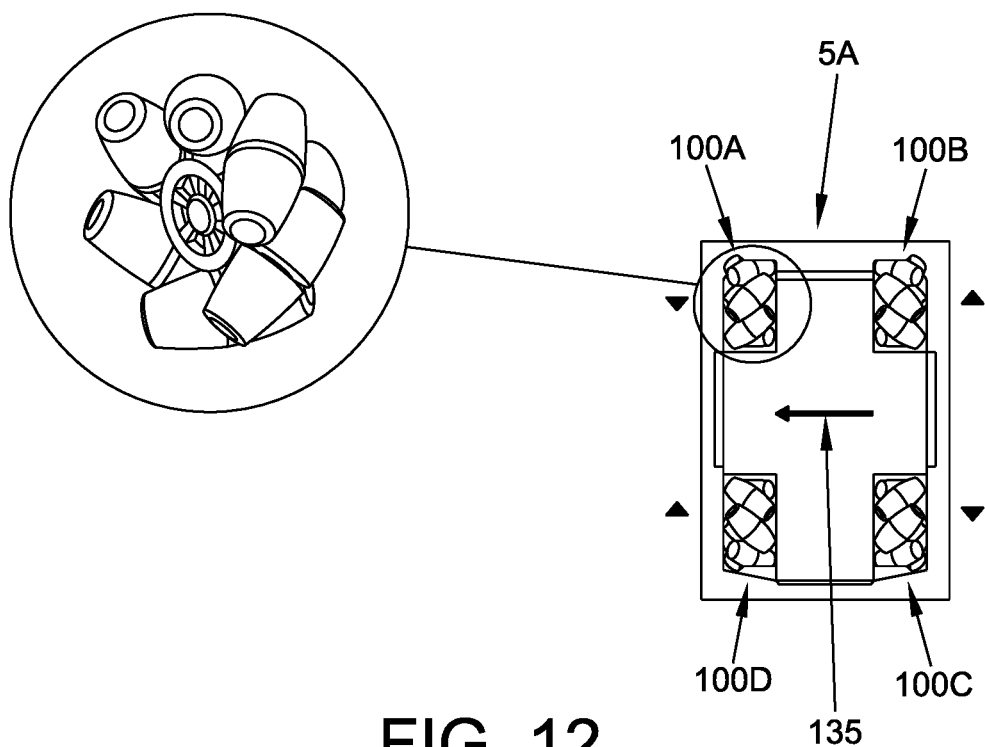

By way of still further example but not limitation, and looking now at FIG. 12, when it is desired to move mobile CT imaging system 5A in the direction indicated by arrow 135 (i.e., the direction opposite arrow 130 of FIG. 11, but still in the direction of the short axis of mobile CT imaging system 5A, such as may be the case when moving mobile CT imaging system 5A during scanning), mecanum wheels 100A and 100C are moved in a first direction (i.e., perpendicular to the direction of arrow 135 and "down" according to the frame of reference of FIG. 12) and mecanum wheels 100B and 100D are moved in a second, opposite direction (i.e., perpendicular to the direction of arrow 135 and "up" according to the frame of reference of FIG. 12). Again, as noted above, due to the disposition of rollers 105 relative to central hub 110 of each of mecanum wheels 100A, 100B, 100C and 100D, the coordinated rotation of mecanum wheels 100A, 100B, 100C and 100D in this manner permits movement in a direction parallel to the longitudinal axes of axles 115 without requiring pivoting (i.e., "steering") of mecanum wheels 100A, 100B, 100C, 100D relative to omnidirectional powered drive unit 95.

Figure 13:
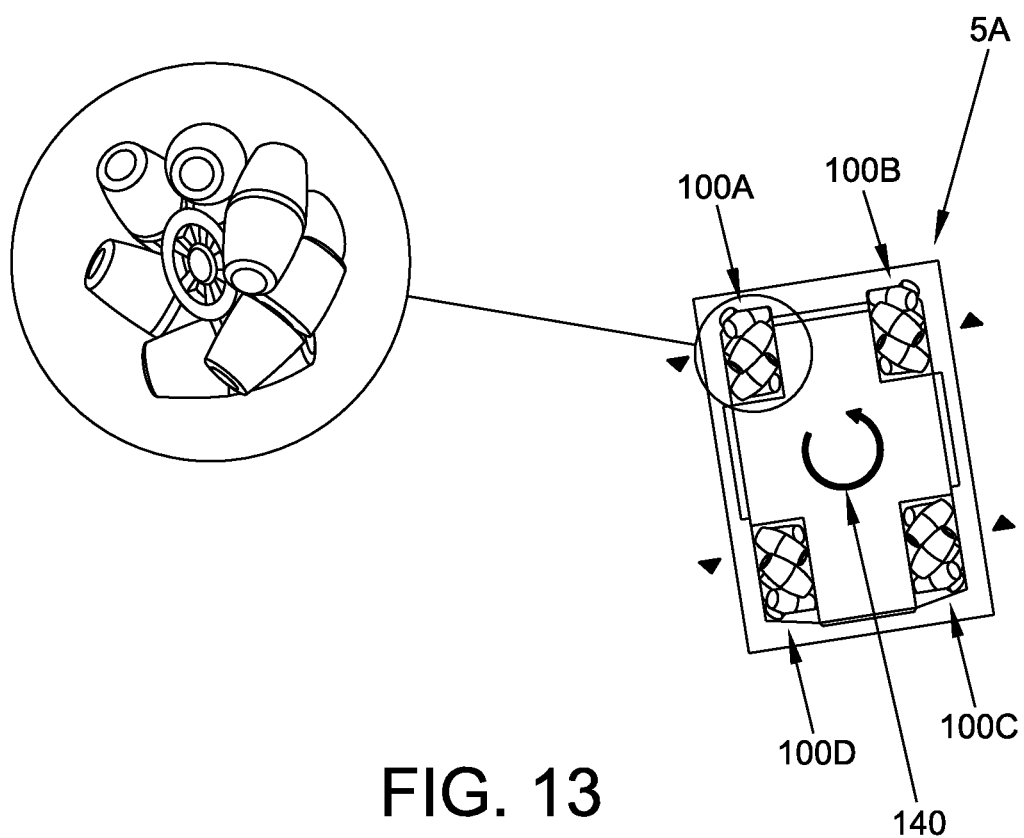

By way of further example but not limitation, and looking now at FIG. 13, when it is desired to rotate mobile CT imaging system 5A in the direction indicated by arrow 140 (such as may be the case when moving mobile CT imaging system 5A over long distances or correcting movement of mobile CT imaging system 5A to re-align with a desired scan path during scanning), mecanum wheels 100A and 100D are moved in a first direction (i.e., "down" according to the frame of reference of FIG. 13) and mecanum wheels 100B and 100C are moved in a second, opposite direction (i.e., "up" according to the frame of reference of FIG. 13). Again, as noted above, due to the disposition of rollers 105 relative to central hub 110 of each of mecanum wheels 100A, 100B, 100C and 100D, the coordinated rotation of mecanum wheels 100A, 100B, 100C and 100D in this manner permits rotation of mobile CT imaging system 5A without requiring pivoting (i.e., "steering") of mecanum wheels 100A, 100B, 100C, 100D relative to omnidirectional powered drive unit 95.

Figure 14:
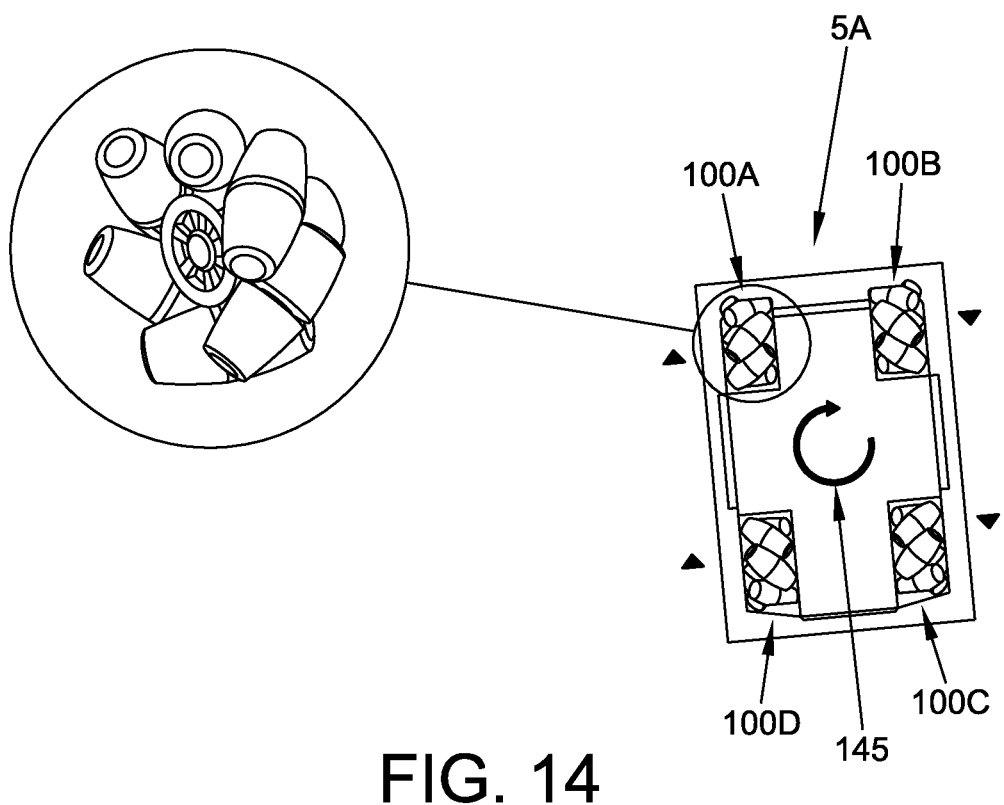

By way of still further example but not limitation, and looking now at FIG. 14, when it is desired to rotate mobile CT imaging system 5A in the direction indicated by arrow 145 (such as may be the case when moving mobile CT imaging system 5A over long distances or correcting movement of mobile CT imaging system 5A to re-align with a desired scan path during scanning), mecanum wheels 100A and 100D are moved in a first direction (i.e., "up" according to the frame of reference of FIG. 14) and mecanum wheels 100B and 100C are moved in a second, opposite direction (i.e., "down" according to the frame of reference of FIG. 14). Again, as noted above, due to the disposition of rollers 105 relative to central hub 110 of each of mecanum wheels 100A, 100B, 100C and 100D, the coordinated rotation of mecanum wheels 100A, 100B, 100C and 100D in this manner permits rotation of mobile CT imaging system 5A without requiring pivoting (i.e., "steering") of mecanum wheels 100A, 100B, 100C, 100D relative to omnidirectional powered drive unit 95.

It should be appreciated that the coordinated movements of mecanum wheels 100 (i.e., mecanum wheels 100A, 100B, 100C, 100D) discussed above are not intended to be limiting, and that other coordinated movements of mecanum wheels 100 are possible in order to achieve other desired movement of mobile CT imaging system 5A. By way of example but not limitation, certain mecanum wheels 100 may be rotated while others do not rotate, the relative speed of rotation of one or more of the mecanum wheels relative to others of the mecanum wheels may be varied, etc.

Thus, mecanum wheels 100 are essentially motorized wheels which, when operated in a coordinated fashion, can provide omnidirectional drive. Inasmuch as mecanum wheels 100 provide omnidirectional drive, the mecanum wheels allow mobile CT imaging system 5A to move in an infinitely-adjustable, omnidirectional manner, whereby to compensate for any lateral walk (or drift) which may occur during the course of a scan due to floor tilt.

By way of example but not limitation, if mobile CT imaging system 5A begins to walk (or "drift") laterally during the course of scanning, the direction and/or speed of rotation of one or more of mecanum wheels 100 may be adjusted so as to re-align mobile CT imaging system 5A with the scan path (i.e., with the bed or gurney which is supporting the patient).

It should be appreciated that the provision of an omnidirectional powered drive unit 95 comprising a plurality of independently drivable mecanum wheels 100 allows for a wide range of movement for mobile CT imaging system 5A, over both long distances (e.g., during transport of mobile CT imaging system 5A from one area of a hospital to another area of the hospital) and short distances (e.g., during scanning). At the same time, omnidirectional powered drive unit 95 permits extremely fine adjustment of the direction (and/or speed) of movement of mobile CT imaging system 5A, whereby to permit real-time re-alignment of mobile CT imaging system 5A with a scan path during scanning.

Use Of Omnidirectional Powered Drive 95

In accordance with the present invention, ominidirectional powered drive unit 95 can be used to move mobile CT imaging system 5A as follows. Initially, mobile CT imaging system 5A is maneuvered about a room using its independently drivable mecanum wheels 100 so that mobile CT imaging system 5A is properly aligned with the patient who is to be scanned, i.e., with the bed or gurney upon which the patient is lying. Thereafter, when scanning is to be commenced, omnidirectional powered drive 95 uses its independently drivable mecanum wheels 100 to move mobile CT imaging system 5A precisely relative to the patient during scanning.

More particularly, during scanning, mecanum wheels 100 are driven so as to move mobile CT imaging system 5A along the scan path. If mobile CT imaging system 5A begins to deviate from the scan path during the course of scanning (e.g., due to imperfections in the floor over which mecanum wheels 100 move), one or more of the mecanum wheels 100 can be selectively rotated (e.g., in the same direction or in opposite directions, at the same speed or at varying speeds, etc. as discussed above) so as to re-align mobile CT imaging system 5A with the scan path. It should be appreciated that such adjustments may be effected in real-time so as to dynamically adjust the movement of mobile CT imaging system 5A during scanning. As a result, mobile CT imaging system 5A can better track the scan path during scanning.

Application to Other Types of Scanning Systems

It should be appreciated that the present invention is not limited to use in medical applications or, indeed, to use with CT machines. Thus, for example, the present invention may be used in connection with mobile CT machines used for non-medical applications, e.g., with mobile CT machines used to scan inanimate objects. Furthermore, the present invention may be used with non-CT-type mobile scanning systems. Thus, for example, the present invention may be used in conjunction with mobile SPECT machines, mobile MRI machines, mobile PET machines, mobile X-ray machines, etc., i.e., wherever the mobile scanning machine may require close tracking to a scan path.

MODIFICATIONS

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. An imaging system comprising:
a scanner;
a transport mechanism mounted to the base of the scanner, wherein the transport mechanism comprises:
  a gross movement mechanism for transporting the scanner relatively quickly across room distances; and
  a fine movement mechanism for moving the scanner precisely, relative to the object being scanned, during scanning; and
  apparatus for selectively causing the gross movement mechanism or the fine movement mechanism to engage the floor;
  wherein the gross movement mechanism comprises a plurality of wheels configured to provide omnidirectional drive; and
  wherein the fine movement mechanism comprises a plurality of independently powered wheels; and
  a drive bar for controlling operation of the plurality of wheels of the gross movement mechanism;
  wherein the drive bar comprises a left side and a right side;
  wherein the drive bar is configured to detect the following motions of the drive bar: left side forward, left side back, left side up, left side down, right side forward, right side back, right side up and right side down; and
  further wherein the drive bar is configured such that:
    (i) when the right side of the drive bar and the left side of the drive bar are both pressed forwardly, the plurality of wheels of the gross movement mechanism move the imaging system forwardly;
    (ii) when the right side of the drive bar and the left side of the drive bar are both pulled rearwardly, the plurality of wheels of the gross movement mechanism move the imaging system rearwardly;
    (iii) when the right side of the drive bar is pressed forwardly and the left side of the drive bar is pulled rearwardly, the plurality of wheels of the gross movement mechanism rotate the imaging system to the left;
    (iv) when the right side of the drive bar is pulled rearwardly and the left side of the drive bar is pushed forwardly, the plurality of wheels of the gross movement mechanism rotate the imaging system to the right;
    (v) when the right side of the drive bar is lifted upwardly and the left side of the drive bar is pushed downwardly, the plurality of wheels of the gross movement mechanism move the imaging system laterally to the left; and
    (vi) when the right side of the drive bar is pushed downwardly and the left side of the drive bar is pulled upwardly, the plurality of wheels of the gross movement mechanism move the imaging system laterally to the right.

2. An imaging system according to claim 1 wherein the wheels of the gross movement mechanism comprise a plurality of mecanum wheels.

3. An imaging system according to claim 2 wherein the wheels of the gross movement mechanism comprise four mecanum wheels.

4. An imaging system according to claim 1 wherein the wheels of the gross movement mechanism comprise steerable powered castors.

5. An imaging system according to claim 1 further comprising a collision sensor system for detecting the presence of an obstacle in the drive path of the imaging system or alongside the imaging system.

6. An imaging system according to claim 5 wherein, when the collision sensor system detects the presence of an obstacle in the drive path of the imaging system or alongside the imaging system, the collision sensor system responds by causing at least one of the following actions: sounding an alarm and automatically decreasing the speed of the gross movement mechanism.

7. An imaging system according to claim 1 wherein the scanner comprises a CT machine.

8. A method for scanning an object, the method comprising:
providing an imaging system, the imaging system comprising:
  a scanner;

a transport mechanism mounted to the base of the scanner, wherein the transport mechanism comprises:
  a gross movement mechanism for transporting the scanner relatively quickly across room distances; and
  a fine movement mechanism for moving the scanner precisely, relative to the object being scanned, during scanning; and
  apparatus for selectively causing the gross movement mechanism or the fine movement mechanism to engage the floor;
  wherein the gross movement mechanism comprises a plurality of wheels configured to provide omnidirectional drive; and
  wherein the fine movement mechanism comprises a plurality of independently powered wheels; and
a drive bar for controlling operation of the plurality of wheels of the gross movement mechanism;
  wherein the drive bar comprises a left side and a right side;
  wherein the drive bar is configured to detect the following motions of the drive bar: left side forward, left side back, left side up, left side down, right side forward, right side back, right side up and right side down; and
  further wherein the drive bar is configured such that:
    (i) when the right side of the drive bar and the left side of the drive bar are both pressed forwardly, the plurality of wheels of the gross movement mechanism move the imaging system forwardly;
    (ii) when the right side of the drive bar and the left side of the drive bar are both pulled rearwardly, the plurality of wheels of the gross movement mechanism move the imaging system rearwardly;
    (iii) when the right side of the drive bar is pressed forwardly and the left side of the drive bar is pulled rearwardly, the plurality of wheels of the gross movement mechanism rotate the imaging system to the left;
    (iv) when the right side of the drive bar is pulled rearwardly and the left side of the drive bar is pushed forwardly, the plurality of wheels of the gross movement mechanism rotate the imaging system to the right;
    (v) when the right side of the drive bar is lifted upwardly and the left side of the drive bar is pushed downwardly, the plurality of wheels of the gross movement mechanism move the imaging system laterally to the left; and
    (vi) when the right side of the drive bar is pushed downwardly and the left side of the drive bar is pulled upwardly, the plurality of wheels of the gross movement mechanism move the imaging system laterally to the right;
  transporting the scanner to the object, across room distances, using the gross movement mechanism; and
  while moving the scanner precisely, relative to the object, with the fine movement mechanism, scanning the object.

9. A method according to claim 8 wherein the wheels of the gross movement mechanism comprise a plurality of mecanum wheels.

10. A method according to claim 9 wherein the wheels of the gross movement mechanism comprise four mecanum wheels.

11. A method according to claim 8 wherein the wheels of the gross movement mechanism comprise steerable powered castors.

12. A method according to claim 8 further comprising a collision sensor system for detecting the presence of an obstacle in the drive path of the imaging system or alongside the imaging system.

13. A method according to claim 12 wherein, when the collision sensor system detects the presence of an obstacle in the drive path of the imaging system or alongside the imaging system, the collision sensor system responds by causing at least one of the following actions: sounding an alarm and automatically decreasing the speed of the gross movement mechanism.

14. A method according to claim 8 wherein the scanner comprises a CT machine.

15. An imaging system according to claim 1 wherein the drive bar comprises:
  a first sensing element for detecting forward/backward movement of the right side of the drive bar;
  a second sensing element for detecting forward/backward movement of the left side of the drive bar; and
  a third sensing element for detecting upward/downward movement of the right side of the drive bar and the left side of the drive bar.

16. An imaging system according to claim 15 wherein the first sensing element comprises four sensors, the second sensing element comprises four sensors, and the third sensing element comprises two sensors.

17. A method according to claim 8 wherein the drive bar comprises:
  a first sensing element for detecting forward/backward movement of the right side of the drive bar;
  a second sensing element for detecting forward/backward movement of the left side of the drive bar; and
  a third sensing element for detecting upward/downward movement of the right side of the drive bar and the left side of the drive bar.

18. A method according to claim 17 wherein the first sensing element comprises four sensors, the second sensing element comprises four sensors, and the third sensing element comprises two sensors.

* * * * *